US008709451B2

(12) United States Patent
Nam et al.

(10) Patent No.: US 8,709,451 B2
(45) Date of Patent: Apr. 29, 2014

(54) STABLE NANOEMULSIONS FOR ULTRASOUND-MEDIATED DRUG DELIVERY AND IMAGING

(75) Inventors: Kweon-Ho Nam, Jeju (KR); Natalya Y. Rapoport, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 103 days.

(21) Appl. No.: 13/008,951

(22) Filed: Jan. 19, 2011

(65) Prior Publication Data
US 2011/0177005 A1 Jul. 21, 2011

Related U.S. Application Data

(60) Provisional application No. 61/402,074, filed on Aug. 23, 2010, provisional application No. 61/296,516, filed on Jan. 20, 2010.

(51) Int. Cl.
*A61K 9/107* (2006.01)
(52) U.S. Cl.
USPC ........................................... 424/400; 424/9.5
(58) Field of Classification Search
None
See application file for complete search history.

(56) References Cited

U.S. PATENT DOCUMENTS

| 4,570,004 | A | 2/1986 | Lagow et al. |
| 7,179,449 | B2 * | 2/2007 | Lanza et al. ............... 424/9.321 |
| 2007/0026024 | A1 | 2/2007 | Drees |
| 2007/0184076 | A1 | 8/2007 | Unger et al. |
| 2008/0297151 | A1 * | 12/2008 | Hirata et al. .................. 324/307 |
| 2009/0117177 | A1 | 5/2009 | Rapoport et al. |
| 2010/0178305 | A1 | 7/2010 | Rapoport |

FOREIGN PATENT DOCUMENTS

| WO | WO 2006127953 A2 * | 11/2006 |
| WO | 2008/070490 | 6/2008 |
| WO | 2009/009105 | 1/2009 |
| WO | 2009/051997 | 4/2009 |
| WO | 2009/073193 | 6/2009 |
| WO | 2009/151788 | 12/2009 |

OTHER PUBLICATIONS

Rapoport et al., "Controlled and targeted tumor chemotherapy by ultrasound-activated nanoemulsions/microbubbles", Journal Controlled Release, vol. 138, pp. 268-276, 2009, Elservier B.V., Salt Lake City, UT.
Mohan et al., "Doxorubicin as a Molecular Nanotheranostic Agent: Effect of Doxorubicin Encapsulation in Micelles or Nanoemulsions on the Ultrasound-Mediated Intracellular Delivery and Nuclear Trafficking", Molecular Pharmaceutics, vol. 7, No. 6, pp. 1959-1973, Oct. 19, 2010, American Chemical Society, Salt Lake City, UT.
Rapoport et al., "Ultrasonic Nanotherapy of Pancreatic Cancer: Lessons from Ultrasound Imaging", Molecular Pharmaceutics, vol. 7, No. 1, pp. 22-31, Nov. 9, 2009, American Chemical Society, Salt Lake City, UT.
Lanza et al., "Targeted Antiproliferative Drug Delivery to Vascular Smooth Muscle Cells With a Magnetic Resonance Imaging Nanoparticle Contrast Agent: Implications for Rational Therapy of Restenosis", Circulation, pp. 2842-2847, Aug. 24, 2002, American Heart Association, Inc., Dallas, TX.
Flogel et al., "In Vivo Monitoring of Inflammation After Cardiac and Cerebral Ischemia by Fuorine Magnetic Resonance Imaging", Circulation, pp. 1-9, Jun. 23, 2008, American Heart Association, Inc., Dallas, TX.
Partlow et al., "19F Magnetic Resonance Imaging for Stem/Progenitor Cell Tracking With Multiple Unique Perfluorocarbon Nanobeacons", The FASEB Journal, vol. 21, pp. 1647-1654, Jun. 2007, FASEB, USA.
Janjic et al., "Self-delivering Nanoemulsions for Dual Fluorine-19 MRI and Fluorescence Detection", JACS Articles, vol. 130, No. 9, pp. 2832-2841, 2008, American Chemical Society, Pittsburg, PA.
Soman et al., "Sythesis and Characterization of Stable Fluorocarbon Nanostructures as Drug Delivery Vehicles for Cytolytic Peptides", NANO Letters, vol. 8, No. 4, pp. 1131-1136, 2008, American Chemical Society, St. Louis, MO.
Psychoudakis et al. "Potential of Microbubbles for Use as Point Targets in Phase Aberration Correction", IEEE, vol. 51, No. 12, Dec. 2004, IEEE, USA.
Lo et al. "Acoustic Droplet Vaporization Threshold: Effects of Pulse Duration and Contrast Agent", IEEE, vol. 54, No. 5, May 2007, IEEE, USA.
Lim et al. "Multifunctional Perfluorocarbon Nanoemulsions for 19F-based Magnetic Resonance and Near-Infrared Optical Imaging of Dendritic Cells", ChemComm, pp. 6952-6954, Oct. 2009, The Royal Society of Chemistry, UK.
Kaneda et al., "Perfluorocarbon Nanomulsions for Quantitative Molecular Imaging and Targeted Theraputics", Ahnals of Biomedical Engineering, vol. 37, No. 10, pp. 1922-1933, Oct. 2009, Biomedical Engineering Society, St. Louis, MO.
Diaz-Lopez et al., "Liqiud Perfluorocarbons as Contrast Agents for Ultrasonography and 19F-MRI", Pharmaceutical Reasearch, 2009, Springer Science + Business Media, LLC, USA.
Rapoport, et al., "Focused ultrasound-mediated drug delivery to pancreatic cancer in a mouse model", Journal of Therapeutic Ultrasound, 2013, 1:1-11.
Ebner, et al., "Early Assessment of Pulmonary Inflammation by 19F MRI In Vivo", Circulation, Jan. 8, 2010, American Heart Association, Dallas, TX.
Lanza, et al., "A Novel Site-Targeted Ultrasonic Contrast Agent With Broad Biomedical Application", Circulation, 1996 American Heart Association, Dallas, TX.
Rapoport, et al., "Phase-shift nanoemulsion/microbubble platform for ultrasound-mediated drug delivery", 15th European Symposium on Ultrasound Contrast Imaging, Dec. 2009.

* cited by examiner

*Primary Examiner* — Nissa Westerberg
(74) *Attorney, Agent, or Firm* — Gardner, Groff, Greenwald & Villanueva, P.C.

(57) ABSTRACT

Described herein are nanoemulsions comprising (1) at least one fluoro ether and (2) a block copolymer comprising a hydrophilic block and hydrophobic block, wherein the nanoemulsion comprises a therapeutic agent in the nanoemulsion. The nanoemulsions are stable and are excellent drug delivery devices for ultrasound-mediated, image guided drug delivery. Also described herein are methods for using the nanoemulsions to treat tumors and cancers as well as using them as imaging agents.

20 Claims, 19 Drawing Sheets

| | R/G RATIO |
|---|---|
| HOECHST STAIN | |
| HYDROPHILIC DOX IN PBS | 0.59 |
| DEPROTONATED DOX IN PBS | 0.086 |

STABLE NANOEMULSIONS FOR ULTRASOUND-MEDIATED DRUG DELIVERY AND IMAGING

CROSS REFERENCE TO RELATED APPLICATIONS

This application claims priority upon U.S. provisional application Ser. Nos. 61/296,516, filed Jan. 20, 2010, and 61/402,074, filed on Aug. 23, 2010. These applications are hereby incorporated by reference in their entireties for all of their teachings.

ACKNOWLEDGEMENT

The research leading to this invention was funded in part by the National Institutes of Health, Grant Nos. R01EB 1033 and R56EB 1033. The Government has certain rights in this invention.

BACKGROUND

Severe side effects of current tumor chemotherapy are caused by drug attack on healthy tissues. To solve systemic toxicity problems, various drug delivery modalities have been suggested that are commonly based on drug encapsulation in carriers such as liposomes, polymeric micelles, and hollow nanocontainers. These drug carriers are targeted to tumors either passively or actively. Tumor targeting of many carriers is often inefficient because the carriers are too large to extravasate through the inter-endothelial gaps of the tumor. Release of the drugs contained within the carriers is often problematic. Moreover, carriers are often unstable in body fluids, which also limits their application as a drug delivery device. Disclosed herein are stable nanoemulsions and uses thereof as drug delivery devices.

SUMMARY

Described herein are nanoemulsions comprising (1) at least one fluoro ether and (2) a block copolymer comprising a hydrophilic block and hydrophobic block, wherein the nanoemulsion comprises a therapeutic agent in the nanoemulsion. The nanoemulsions are stable and are excellent drug delivery devices for ultrasound-mediated, image guided drug delivery. Also described herein are methods for using the nanoemulsions to treat tumors and cancers as well as imaging agents. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 14 shows Hoechst stain that stains the nuclei of cells. The intracellular uptake of free DOX is higher for hydrophilic DOX compared with deprotonated DOX. Scale bar is 20 μm. Red-to-green (R/G) ratios of the cell fluorescence were averaged over the cells in the field of view (FOV) and tabulated below the Figure. The brightness and contrast ratios of magnified insets of the images were modified to better reveal fluorescence inside the cells nuclei.

DETAILED DESCRIPTION

Figure 1:
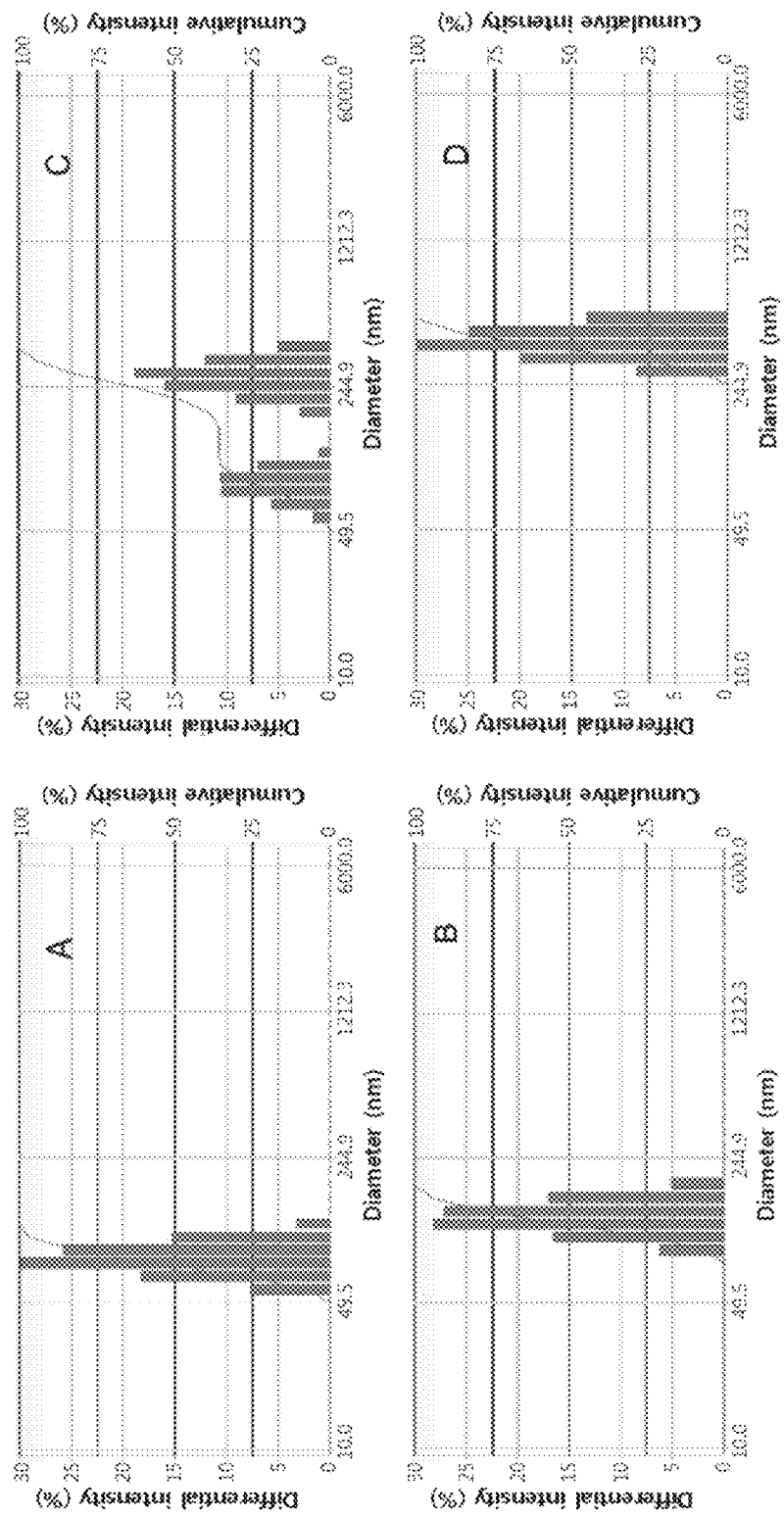
FIG. 1 shows the particle size distribution for (A) empty 5% PEG-PDLA micelles; size distribution parameters: 81.6±14.7; (B) PTX-loaded PEG-PDLA micelles (0.5% PTX/5% PEG-PDLA); size distribution parameters: 129±23.7 nm; (C) nanodroplet formulation (1% PFCE/5% PEG-PDLA); size distribution parameters: peak 1–83.7±14.3 nm (33%); peak 2–275.1±50.8 nm (67%); (D) 5% PFCE/5% PLA nanodroplets; size distribution parameters: 392±65 nm.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a therapeutic agent" includes two or more such therapeutic agents, and the like.

"Optional" or "optionally" means that the subsequently described event or circumstance can or cannot occur, and that the description includes instances where the event or circumstance occurs and instances where it does not. For example, the phrase "optionally a second therapeutic agent" means that the second therapeutic agent may or may not be present in the compositions used for the methods described herein.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "alkoxy group" as used herein is defined as RO—, where R is an alkyl group or aryl group defined herein.

The term "halogenated group" is any organic group such as, for example, an alkyl group or aryl group, that possesses at least one halogen (F, Cl, Br, I).

"Treating" or "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "preventing" refers to a reduction or delay in the onset of metastasis and does not require absolute preclusion.

"Therapeutic agent" refers to a chemical compound, a hormone, or a biological molecule including nucleic acids, peptides, proteins, and antibodies that can be used to treat a pre-existing condition or reduce the symptoms of the condition.

"Nanoemulsion" refers either to nanodroplets that are less than 1500 nm, or more preferably less than 1000 nm in diameter, which are capable of encapsulating a therapeutic agent.

"Subject" refers to mammals including, but not limited to, humans, non-human primates, sheep, dogs, rodents (e.g., mouse, rat, etc.), guinea pigs, cats, rabbits, cows, and non-mammals including chickens, amphibians, and reptiles, who are at risk for or have been diagnosed with a tumor and benefits from the methods and compositions described herein.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

It is understood that any given particular aspect of the disclosed compositions and methods can be easily compared to the specific examples and embodiments disclosed herein. By performing such a comparison, the relative efficacy of each particular embodiment can be easily determined Particularly preferred compositions and methods are disclosed in the Examples herein, and it is understood that these compositions and methods, while not necessarily limiting, can be performed with any of the compositions and methods disclosed herein.

Variables such as n, y, $R^1$, $R^2$, $X^1$, and $X^2$ used throughout the application are the same variables as previously defined unless stated to the contrary.

I. Nanoemulsions and Preparation Thereof

Described herein are stable nanoemulsions useful as drug delivery devices and imaging agents. In one aspect, the nanoemulsion comprises (1) at least one fluoro ether and (2) a block copolymer comprising a hydrophilic block and hydrophobic block, wherein the nanoemulsion comprises a therapeutic agent encapsulated in the nanoemulsion. Each component is discussed in detail below.

The term "fluoro ether" as used herein is any organic ether possessing at least one fluoro group. Depending upon the application, the fluoro ether can contain multiple fluoro groups. For example, all of the hydrogen atoms of the organic ether can be substituted with a fluoro group. In one aspect, the fluoro ether described herein includes a linear fluoro ether having the following I:

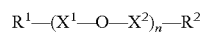

$$R^1\text{—}(X^1\text{—}O\text{—}X^2)_n\text{—}R^2 \qquad \text{I}$$

wherein $X^1$ and $X^2$ are, independently, $(CF_2)_y$, $(CHF)_y$, or $(CF_2\text{—}CHF)_y$;

$R^1$ and $R^2$ are, independently hydrogen, an alkyl group, an aryl group, an alkoxy group, a hydroxyl group, or a halogenated group, wherein one or both of $R^1$ and $R^2$ are optionally fluorinated;

O is oxygen;

y is 1, 2, 3, 4, 5, 6, 7, 8, 9, 10, 11, 12, 13, 14, 15, 16, 17, 18, 19, or 20; and n is 1, 2, 3, 4, 5, 6, 7, 8, 9, 10, 11, 12, 13, 14, 15, 16, 17, 18, 19, or 20, wherein the fluoro ether has at least 16 fluorine atoms.

For imaging purposes, with respect to the fluorine atoms, the fluoro ether should be symmetrical. For example, referring to formula I above, $X^1$ and $X^2$ are the same fluoro groups. In certain aspects, $R^1$ and $R^2$ are also identical. When the fluoro groups are symmetrical, the $^{19}F$ MR spectrum is not broad and, thus, useful in imaging the nanoemulsion. The number of fluorine atoms present in the fluoro ether can also determine the intensity of the signal in the $^{19}F$ MR spectrum. The fluoro ether has at least 16 fluorine atoms, at least 18 fluorine atoms, or at least 20 fluorine atoms. In one aspect, the linear fluoro ether has the formula $R^1O—[CF_2—CF_2—O—]_n—R^2$, where n is at least 5 and $R^1$ and $R^2$ do not contain fluorine. In other aspects, the fluoro ether can be oligomers or polymers. For example, referring to formula I, n can be greater than 20.

In one aspect, the fluoro ether is a perfluoro crown ether, or a combination thereof. Crown ethers are heterocyclic chemical compounds that are composed of a ring containing several ether groups. The most common crown ethers are oligomers of ethylene oxide the repeating unit being ethyleneoxy, i.e., —$CH_2CH_2O$—. However, other alkylene oxides can be present in the crown ether including, but not limited to, propylene oxide, butylene oxide, and the like. Examples of this series of compounds are the tetramer (n=4), the pentamer (n=5), the hexamer (n=6), the heptamer (n=7), the octamer (n=8), the decamer (n=10), and the like. Similar to the linear fluoro ethers described above, the perfluoro crown ether has at least 16 symmetrical fluorine atoms. In other aspects, perfluoro crown ether is any crown ether with all hydrogen atoms substituted with fluorine atoms. Examples of perfluoro crown ethers include, but are not limited to, perfluoro 12-crown-4 ether, perfluoro 15-crown-5 ether, perfluoro 18-crown-6 ether, perfluoro 21-crown-7 ether, perfluoro dibenzo-18-crown-6 ether, perfluoro diaza-18-crown-6 ether, or any combination thereof.

Turning to the block copolymer, it includes a hydrophilic block and a hydrophobic block. In one aspect, the hydrophilic block can include a poly(alkylene oxide), a polyvinyl polymer such as polyvinyl pyrrolidone, or any combination thereof. In certain aspects, the hydrophilic block includes a poly(alkylene oxide). In some aspects, the poly(alkylene oxide) can have a molecular weight ranging from 500 to 10,000 Da, from 1,000 to 8,000 Da, from 1,500 to 5,000 Da, or from 1,500 to 2,500 Da. For example, the poly(alkylene oxide) can include a polyethylene oxide, a polypropylene oxide, a polybutylene oxide, a polypentylene oxide, or a combination thereof. In another aspect, the poly(alkylene oxide) is a triblock copolymer such as PEO-PPO-PEO or PPO-PEO-PPO. In one aspect, the poly(alkylene oxide) is polyethylene oxide having a molecular weight of 1000 Da, 2000 Da, 3000 Da, 4000 Da, or 5000 Da.

In some aspects, the hydrophobic block is a polymer having a molecular weight ranging from 500 to 1000 Da, from 500 to 1500 Da, from 500 to 2000 Da, from 500 to 2500 Da, from 500 to 3000 Da, from 500 to 3500 Da, from 500 to 4000 Da, from 500 to 4500 Da, from 500 to 5000 Da, from 500 to 5500 Da, from 500 to 6000 Da, from 500 to 6500 Da, from 500 to 7000 Da, from 500 to 7500 Da, from 500 to 8000 Da, from 500 to 8500 Da, from 500 to 9000 Da, from 500 to 9500 Da, from 500 to 10000 Da, from 500 to 10500 Da, from 500 to 11000 Da, from 500 to 11500 Da, or from 500 to 12000 Da. In one aspect, the hydrophobic block can include, but is not limited to, a polymer of lactic acid, a polylactone, or a combination thereof. Examples of the lactic acid that are present in the block copolymer can include a poly(l)lactic acid, a poly(d,l)lactic acid, a poly(d)lactic acid, or a combination thereof. In some aspects, the molecular weight of the poly(l) lactic acid, poly(d,l)lactic acid, poly(d)lactic acid, or a combination thereof can range from 500 to 1000 Da, from 500 to 1500 Da, from 500 to 2000 Da, from 500 to 2500 Da, from 500 to 3000 Da, from 500 to 3500 Da, from 500 to 4000 Da, from 500 to 4500 Da, from 500 to 5000 Da, from 500 to 5500 Da, from 500 to 6000 Da, from 500 to 6500 Da, from 500 to 7000 Da, from 500 to 7500 Da, from 500 to 8000 Da, from 500 to 8500 Da, from 500 to 9000 Da, from 500 to 9500 Da, from 500 to 10000 Da, from 500 to 10500 Da, from 500 to 11000 Da, from 500 to 11500 Da, or from 500 to 12000 Da. In some aspects, the molecular weight of the poly(l)lactic acid, poly(d,l)lactic acid, poly(d)lactic acid, or a combination thereof can range from 3000 Da to 5000 Da in molecular weight. In one aspect, the second polymer is poly(l)lactic acid having a molecular weight of 4700 Da.

Examples of the lactone that are present in the block copolymer can include polycaprolactone. In some aspects, the molecular weight of the polycaprolactone can range from 100 to 1000 Da, from 100 to 1500 Da, from 100 to 2000 Da, from 100 to 2500 Da, from 100 to 3000 Da, from 100 to 3500 Da, from 100 to 4000 Da, from 100 to 4500 Da, 100 to 5000 Da, 100 to 6000 Da, 100 to 7000 Da, 100 to 8000 Da, 100 to 9000 Da, 100 to 10000 Da, 100 to 11000 Da, or from 100 to 12000 Da. In some aspects, the molecular weight of the polycaprolactone can range from 2000 Da to 3000 Da. In one aspect, the second polymer is polycaprolactone having a molecular weight of 2600 Da.

In some aspects, the nanoemulsions include nanosized micelles and nanodroplets that have diameters that are less than about 1500 nm, about 1400 nm, about 1300 nm, about 1200 nm, about 1100 nm, about 1050 nm, about 1000 nm, about 950 nm, about 900 nm, about 850 nm, about 800 nm, about 750 nm, about 700 nm, about 650 nm, about 600 nm, about 550 nm, about 500 nm, about 450 nm, about 400 nm, about 350 nm, about 300 nm, about 250 nm, about 200 nm, about 150 nm, about 100 nm, about 90 nm, about 80 nm, about 70 nm, about 60 nm, about 50 nm, about 40 nm, about 30 nm, about 20 nm, or about 10 nm. In some aspects, the micelles have diameters ranging from about 20 nm to about 150 nm. In some aspects, the micelles have diameters ranging from about 20 nm to about 100 nm. In some aspects, the nanodroplets have diameters ranging from about 20 nm to about 500 nm, from about 30 nm to about 400 nm, or from about 30 nm to about 300 nm.

The nanoemulsions described herein are compositions having a hydrophilic outer shell composed of the hydrophilic block of the block copolymer, and lipophilic inner shell composed on the hydrophobic block of the block copolymer, and a lipophilic inner core composed of the fluoro ether. As will be discussed in greater detail below, the nanoemulsions make it possible to efficiently transport lipophilic therapeutic agents or drugs to tumors. Due to the defective tumor's vasculature, the nanoemulsions can be extravasated into the tumor. In one aspect, at least one therapeutic agent is encapsulated within the lipophilic core of the nanoemulsion. In some aspects, the therapeutic agent can include lipophilic drugs that have a low aqueous solubility. For example, these therapeutic agents, can include chemotherapeutic drugs, hormones, or any other biologically or chemically active drugs, which include nucleic acids, peptides, proteins, and/or antibodies, that can be used to treat a condition such as various tumors and cancers. In some aspects, the therapeutic agent can include, but is not limited to, paclitaxel, doxorubicin, adriamycin, cisplatin, taxol, methotrexate, 5-fluorouracil, betulinic acid, amphotericin B, diazepam, nystatin, propofol, testosterone, estrogen, prednisolone, prednisone, 2,3 mercaptopropanol, progesterone, multiple drug resistant (MDR) suppressing agents, or any combination thereof. In some aspects, the therapeutic agent can include, but is not limited to, paclitaxel, doxorubicin, or any combination thereof. For example, in one aspect the therapeutic agent encapsulated in the nanoemulsion can include only paclitaxel. In some aspects, the therapeutic agent encapsulated in the nanoemulsion includes at least paclitaxel. In another aspect, the therapeutic agent encapsulated in the nanoemulsion can include only doxorubicin. In some aspects, the therapeutic agent encapsulated in the nanoemulsion includes at least doxorubicin. In some aspects, the therapeutic agent encapsulated in the nanoemulsion includes at least paclitaxel and doxorubicin.

The nanoemulsions described herein can also be modified to include a targeting moiety. Such targeting moieties can be advantageously used to target specific tissues and cells. In certain aspects, the nanoemulsions are modified on the hydrophilic outer surface of the nanoemulsion to include the targeting moiety. In certain aspects, the nanoemulsions are modified on the hydrophilic outer surface of the nanoemulsion to include the targeting moiety by incorporating PEG-phospholipids into the block copolymer nanodroplet shell. The targeting moiety may include a ligand specific for particular tumors or a ligand that is capable of targeting tumor tissue without damaging normal, non-tumor tissue. In one aspect, the targeting moiety, which includes but is not limited to a target ligand, assists the nanoemulsion in finding the targeted cells or tissue. A ligand may be any compound of interest which will bind to another compound, such as a receptor.

The nanoemulsions described herein can also include PLURONIC® polyoxyethylene-polyoxypropylene-polyoxyethylene triblock copolymers. An example of PLURONIC® triblock copolymer includes, but is not limited to, PLURONIC® L-61, PLURONIC® 105, PLURONIC® 85 or any combination thereof. PLURONIC® L-61 has been used in a SP1049C (micellar doxorubicin formulation) as a sensitizer of multidrug resistant cells (V. Alakhov et al., Block copolymer based formulations of doxorubicin. From cell screen to clinical trials. Colloids and Surfaces B: Biointerfaces 16 (1999) 113-134). In this aspect, by incorporating PLURONIC® triblock copolymers within the nanoemulsions, the nanoemulsion's sensitivity to low-frequency ultrasonic radiation may increase due to an increase in nanodroplet size; cancer cell sensitivity may increase due to enhanced sensitivity to hyperthermia, due to suppression of multidrug resistance, and due to more efficient delivery of therapeutic agents to the tumor may take place. In a further aspect, as stated above, the PLURONIC® triblock copolymers may further function as a MDR suppressing agent. In some aspects, PLURONIC® triblock copolymers such as PLURONIC® L-61 can be incorporated into the nanoemulsion and act to suppress drug resistance and kill MDR tumors due to enhanced tumor's hyperthermia sensitivity.

In one aspect, the nanoemulsions described herein can include a (1) block copolymer wherein the block copolymer is polyethylene glycol poly(l)lactic acid block copolymer or a polyethylene glycol poly(d,l)lactic acid block, (2) a perfluoro crown ether, such as perfluoro 15-crown-5 ether, and (3) a therapeutic agent. In some aspects, the nanoemulsions described herein can include a polyethylene glycol poly(l)lactic acid block copolymer, a perfluoro crown ether, such as perfluoro 15-crown-5 ether, and a therapeutic agent. In some aspects, the nanoemulsions described herein can be mixtures of (1) a polyethylene glycol poly(l)lactic acid block copolymer and a therapeutic agent and (2) a polyethylene glycol poly(l)lactic acid block copolymer, a perfluoro crown ether, such as perfluoro 15-crown-5 ether, and a therapeutic agent.

In some aspects, the nanoemulsions can include a polyethylene glycol polycaprolactone block copolymer, a perfluoro crown ether, and a therapeutic agent. In some aspects, the nanoemulsions described herein can be mixtures of (1) a polyethylene glycol polycaprolactone block copolymer and a therapeutic agent and (2) a polyethylene glycol polycaprolactone block copolymer, a perfluoro crown ether, and a therapeutic agent.

In a further aspect, the nanoemulsions include a polyethylene glycol poly(l)lactic acid block copolymer, a perfluoro crown ether, and a therapeutic agent, wherein the therapeutic agent includes paclitaxel, doxorubicin, or any combination thereof. In some aspects, the nanoemulsion includes a polyethylene glycol polycaprolactone block copolymer, a perfluoro crown ether, and a therapeutic agent, wherein the therapeutic agent includes paclitaxel, doxorubicin, or any combination thereof.

In some aspects, the nanoemulsions described herein can include a polyethylene glycol poly(l)lactic acid block copolymer, a perfluoro 15-crown-5 ether, a therapeutic agent, or any combination thereof. In some aspects, the nanoemulsions described herein can include a polyethylene glycol poly(l) lactic acid block copolymer, a perfluoro 15-crown-5 ether, and a therapeutic agent. In some aspects, the nanoemulsions described herein can be mixtures of (1) a polyethylene glycol poly(l)lactic acid block copolymer and a therapeutic agent and (2) a polyethylene glycol poly(l)lactic acid block copolymer, a perfluoro 15-crown-5 ether, and a therapeutic agent.

In some aspects, the nanoemulsions can include a polyethylene glycol polycaprolactone block copolymer, a perfluoro 15-crown-5 ether, and a therapeutic agent. In some aspects, the nanoemulsions can include a polyethylene glycol polycaprolactone block copolymer, a perfluoro 15-crown-5 ether, and a therapeutic agent. In some aspects, the nanoemulsions described herein can be mixtures of (1) a polyethylene glycol polycaprolactone block copolymer and a therapeutic agent and (2) a polyethylene glycol polycaprolactone block copolymer, a perfluoro 15-crown-5 ether, and a therapeutic agent.

In a further aspect, the nanoemulsions include a polyethylene glycol poly(l)lactic acid block copolymer, a perfluoro 15-crown-5 ether, and a therapeutic agent, wherein the therapeutic agent comprises paclitaxel, doxorubicin, or any combination thereof. In some aspects, the nanoemulsion includes a polyethylene glycol polycaprolactone block copolymer, a perfluoro 15-crown-5 ether, and a therapeutic agent, wherein the therapeutic agent comprises paclitaxel, doxorubicin, or any combination thereof.

The nanoemulsions described herein can be prepared without special handling and techniques. In one aspect, the nanoemulsion can be prepared by admixing the block copolymer and fluoro ether in water followed by exposing the mixture to ultrasound. The amount of block copolymer and fluoro ether can vary. Exemplary methods for making the nanoemulsions are provided in the Examples below.

The preparation of nanoemulsions loaded with one or more therapeutic agents also do not involve special handling and techniques. In one aspect, the block copolymer and therapeutic agent are dissolved in a solvent. Examples of solvents useful herein include, but are not limited to, dimethyl sulfoxide (DMSO), tetrahydrorfuran (THF), or dioxane. The amount of therapeutic agent that can be encapsulated in the nanoemulsion can vary. In one aspect, the therapeutic agent can be from 0.1 wt % to 10 wt %. In some aspects, the block copolymer can be from 0.1 wt % to 5 wt %. In one aspect, in the next step the solvent is evaporated and saline is added or the organic solution is dialyzed against saline. Next, the fluoro ether is added and the mixture is exposed to ultrasound. In some aspects, the fluoro ether is from 0.1 vol % to 20 vol % relative to the nanoemulsion volume. Exemplary methods for making the nanoemulsions loaded with a therapeutic agent are provided in the Examples below.

Figure 5:
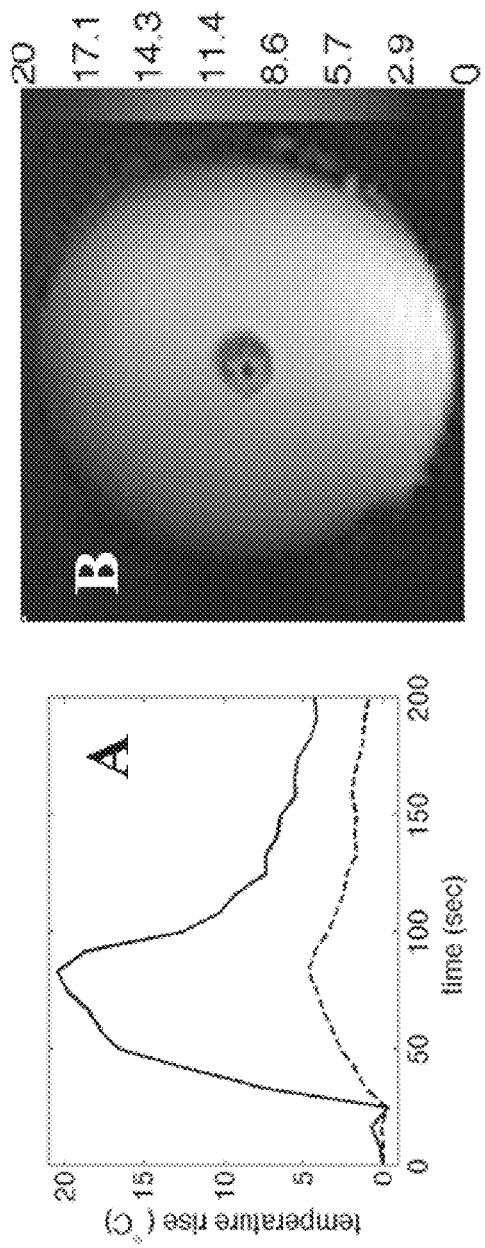
FIG. 5 shows (A) kinetics of temperature rise for the PFCE droplet-loaded (solid line) or empty (dashed line) agarose phantoms. The voxels with the maximum temperature rise are displayed in both cases. Power was applied for 60 s at 40 W (electrical). The maximum power deposition rate was found to be 0.0031 $W/mm^3$ in the phantom impregnated with nanodroplets. This value is consistent with a maximum power intensity of 80 $W/cm^2$ at the focal zone assuming an acoustic efficiency of 45%, an absorption value of 0.04 Np/cm/MHz and a beam size of 2.2×2.2×10 mm. A 2D-GRE sequence was used for thermometry (5 slices, 2×2×3 mm, tacq=8.3 s, TR/TE=65/8 ms, FA=20°, 128×128 matrix). (B) The temperature map at the time when the maximum temperature occurredt ($t_{heat}$=60 s) for the droplet-loaded gel.
Figure 6:
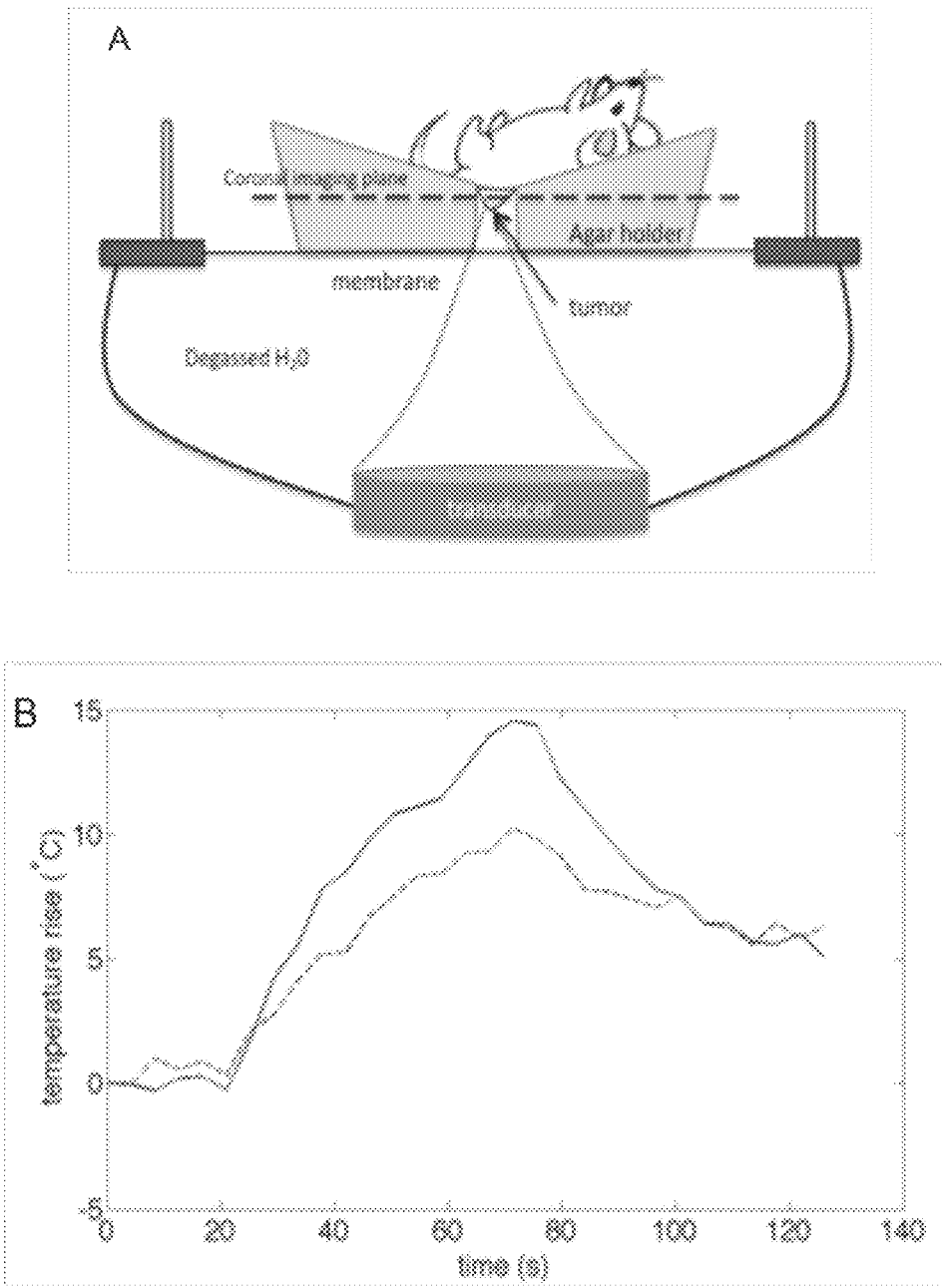
FIG. 6 shows (A) a scheme of FUS experiments; (B) kinetics of FUS-induced temperature rise for the PFCE droplet injected mice; solid line—empty droplets; dashed line— PTX-loaded droplets. Ultrasound beam was steered for 50 s in a circle of 4-mm diameter (8 "points", 200 ms/point, 30 circles per treatment resulting in a 6-s sonication of each "point"). The maximum power deposition rate was 0.001 $W/mm^3$. This value is consistent with a maximum power intensity of 54 $W/cm^2$ at the focal zone assuming an acoustic efficiency of 45%, an absorption value of 0.03 Np/cm/MHz and a beam size of 2.2×2.2×10 mm.

The nanoemulsions described herein possess a number of advantageous properties. For example, due to large differences in acoustic impedance between the fluoro ether and water, the nanoemulsions generate relatively strong ultrasound contrast (see for example FIG. 2). The nanoemulsions readily form microbubbles under therapeutic ultrasound. Despite the presence of the high boiling fluoro ether, the nanoemulsions can be readily converted to microbubbles (see for example FIG. 3), which makes the nanoemulsions effective as a drug delivery device and imaging agent. Moreover, the nanoemulsions undergo stable cavitation both in liquid emulsions and in gel matrices. In certain aspects, this effect was very pronounced under pressures generated by a HIFU transducer and causes and accelerates sample heating (see for examples FIGS. 5 and 6). The microbubbles oscillate and cavitate under the action of tumor-directed low energy therapeutic ultrasound. Therefore, the nanoemulsions described herein can be used as catalysts of tumor ablation or for the MRI-guided HIFU (MRgHIFU) as an activation mechanism for a novel ultrasound-responsive drug delivery The nanoemulsions described herein exhibit high thermal stability, which is important for prolonging their shelf life and facilitate handling. The nanoemulsions also remain stable even during prolonged heating. For example, the nanodroplets can remain stable for 3 to 14 days at temperatures ranging from about 30° C. to about 50° C. Despite thermal stability, the nanoemulsions are sensitive to ultrasound; for example, when perfluoro 15-crown-5 ether having a boiling point of 146° C. was used, the nanoemulsions converted into microbubbles under the action of therapeutic ultrasound (see FIG. 2A).

Due to the stability of the nanoemulsions, in one aspect, a kit having at least one, two, three, four, five, or six of the nanoemulsions as described above is provided. In this aspect, the kit can include, but is not limited to, a vessel or vessels containing the nanoemulsions. In some aspects, the kit includes prepackaged nanoemulsions, which can be sold for commercial use as imaging agents with or without the therapeutic agent. In some aspects, the shelf life of the kit can be from 5 days to 3 months when stored at room temperature (i.e., 20° C. to about 25° C.).

In another aspect, the kit is composed of a first vessel composed of the nanoemulsion without the therapeutic agent and a second vessel composed of a micellar solution of the therapeutic agent. Both vessels can be kept frozen "indefinitely", then thawed before application and mixed. Not wishing to be bound by theory, when the components of the vessels are mixed, the therapeutic agent will migrate from micelles to the surface of the nanodroplets. This will ultimately enhance the delivery of the therapeutic agent.

II. Methods of Use

In some aspects, the compositions and methods described herein may present an efficient targeting chemotherapeutic modality for solid tumors. The methods of treating tumors as described herein can be performed by contacting the tumor with a therapeutic agent encapsulated in a nanoemulsion and exposing the tumor to an ultrasonic radiation at a particular frequency. In some aspects, the tumor can include a multidrug resistant tumor, an inoperable tumor, or a combination thereof. In certain aspects, the tumor includes, but is not limited to, breast cancer, pancreatic cancer, ovarian cancer, prostate cancer, colon cancer or a combination thereof.

The tumor can be contacted with a first nanoemulsion, as described above, by direct injection into the tumor, by subcutaneous injection, by intramuscular injection, or via systemic injection of the nanoemulsion, which includes intravenous injection. When the nanoemulsion is administered systemically, adequate time is given for the nanoemulsion to extravasate into the tumor before exposing the tumor to the first ultrasonic radiation. In some aspects, a time ranging from about 4 hours to about 24 hours is provided to allow the nanoemulsion to extravasate into the tumor. In yet another aspect, a time ranging from about 4 hours to about 8 hours, from about 8 hours to about 14 hours or from about 10 hours to about 24 hours is provided to allow the nanoemulsion to extravasate into the tumor.

In certain aspects, the tumor can be contacted with a second nanoemulsion following contacting the tumor with a first nanoemulsion. For example, the second nanoemulsion can be directly injected into the tumor via intratumoral injection before exposing the tumor to a first ultrasonic radiation. In some aspects, a second nanoemulsion can be directly injected into the tumor after contacting the tumor with the first nanoemulsion but before exposing the tumor to a first ultrasonic radiation. In some aspects, the tumor is immediately exposed to the first ultrasonic radiation after being directly injected with the second nanoemulsion.

Due to the nanoemulsion's stability at 37° C. (e.g., exhibit thermal stability at 37° C. for at least 2 to 5 days), the nanoemulsions described herein are advantageous for the therapeutic purposes mentioned above as well as for imaging purposes. Because of the pharmacodynamics and pharmacokinetics of these nanoemulsions, they can be advantageously used as imaging agents. In one aspect, imaging of a tissue contacted with the nanoemulsions described herein can be conducted by using $^{19}$F MRI. For example, when the nanoemulsion contains perfluoro 15-crown-5 ether, $^{19}$F MRI can be used to image the presence of the nanoemulsion in the subject after administration. In particular, because 20 equivalent fluorine atoms are present in this example (i.e., perfluoro 15-crown-5 ether), it is possible to monitor nanoemulsion distribution within a tumor and normal tissue. In another aspect, imaging of a tissue contacted with these nanoemulsions can be conducted by using ultrasound imaging because of a mismatch in acoustic impedances of the nanoemulsions and endogenous water within a tissue. These impedances generate ultrasound contrast capable of being imaged. In some aspects, ultrasound imaging includes harmonic imaging, doppler imaging such as color doppler, power doppler, and spectral doppler. Thus, the nanoemulsions described herein provide two-modal imaging (i.e., using $^{19}$F MRI and ultrasound imaging).

The imaging of the tumor with the nanoemulsions described herein also aids in the application of the ultrasound to the tumor. By identifying the precise location of the nanoemulsion in the tumor, it is possible to apply a focused beam of ultrasound energy to the tumor in order to convert the nanoemulsion into microbubbles and subsequently release the therapeutic agent in the tumor. For example, using $^{19}$F MRI can pinpoint the location of the nanoemulsions. This approach ultimately results in a much more efficient and effective way to deliver therapeutic agents to tumors.

For example, the methods described herein include treating a tumor by the following steps: (a) contacting the tumor with a therapeutic agent encapsulated in a first nanoemulsion, wherein the first nanoemulsion comprises at least a fluoro containing ether; and (b) exposing the tumor to a first ultrasonic radiation (e.g., in an amount from about 30 kHz to about 20 MHz). In some aspects, a second nanoemulsion can be directly injected into the tumor (i.e., via intratumoral injection) after step (a) but before step (b). In some aspects, the second nanoemulsion can be directly injected into the tumor before step (b).

The nanoemulsions may be used to treat tumor growth, prevent tumor growth, or kill tumors because these nanoemulsions can accumulate and/or extravasate in tumors via, for example, the enhance permeability and retention (EPR) effect. The nanoemulsions can be subsequently converted into microbubbles in situ with ultrasonic radiation, and if a therapeutic agent is present within the nanoemulsion, the therapeutic agent can be released from the nanoemulsion via ultrasound-triggered drug release. The conversion from a nanoemulsion, which includes nanodroplets, to microbubbles is known as acoustic droplet vaporization (ADV); however, other mechanisms of droplet-to-bubble transitions are also possible.

In some aspects, the first ultrasonic radiation can be focused ultrasound (FUS) radiation, unfocused ultrasound, continuous wave (CW) ultrasound radiation, pulsed waved (PW) ultrasound radiation, or any combination thereof. In some aspects, the ultrasonic radiation can be applied by using any one of the following instruments: the Sonablate, the ExAblate, the Ablatherm, or any other Image-Guided HIFU instrument. In some aspects, the first ultrasonic radiation frequency can be from about 30 kHz to about 20 MHz, from about 50 kHz to about 17.5 MHz, from about 70 kHz to about 15 MHz, from about 90 kHz to about 12.5 MHz, from about 150 kHz to about 10 MHz, from about 200 kHz to about 7.5 MHz, from about 250 kHz to about 5 MHz, from about 300 kHz to about 4 MHz, from about 400 kHz to about 3 MHz, or from about 500 kHz to about 1.5 MHz. In some aspects, the first ultrasonic radiation frequency is from about 1 MHz to about 3 MHz. In some aspects, the first ultrasonic radiation frequency has a peak to peak pressure ranging from about 0.5 MPa to about 7 MPa.

The methods described herein can be used to treat subjects having cancer. As described above, these tumors can include, but are not limited to breast tumors, ovarian tumors, pancreatic tumors, prostate cancer, colon cancer, or a combination thereof. In some aspects, the method of treating a tumor in a subject includes injecting a therapeutic agent encapsulated in a nanoemulsion into the subject; exposing the tumor to ultrasonic radiation from about 1 MHz to about 5 MHz to the tumor. In this aspect, the nanoemulsion can be injected intravenously, subcutaneously, intramuscularly, intratumorally, or any combination thereof. In some aspects, this method can be repeated as needed. If desired, the ultrasonic radiation can be less than about 4 MHz, 3.5 MHz, 3 MHz, 2.75 MHz, 2.5 MHz, 2.25 MHz, 2 MHz, 1.75 MHz, 1.5 MHz, 1.25 MHz, 1 MHz, 900 kHz, 800 kHz, 700 kHz, 600 kHz, 500 kHz, 400 kHz, 300 kHz, 200 kHz, 100 kHz, 90 kHz, 80 kHz, 70 kHz, 60 kHz, 50 kHz, 40 kHz, or 30 kHz. If desired, the ultrasonic radiation can range from about 1 MHz to about 9 MHz, from about 1 MHz to about 8.5 MHz, from about 1 MHz to about 8.0 MHz, from about 1 MHz to about 7.5 MHz, from about 1 MHz to about 7.0 MHz, from about 1 MHz to about 6.5 MHz, from about 1 MHz to about 6.0 MHz, from about 1 MHz to about 5.5 MHz, from about 1 MHz to about 5.0 MHz, from about 1 MHz to about 4.5 MHz, from about 1 MHz to about 4.0 MHz, from about 1 MHz to about 3.5 MHz, from about 1 MHz to about 3.0 MHz, from about 1 MHz to about 2.5 MHz, from about 1 MHz to about 2.0 MHz, or from about 1 MHz to about 1.5 mHz. In each of these aspects, the nanoemulsion, which may contain an encapsulated therapeutic agent, can undergo acoustic droplet vaporization (ADV) or other mechanism of droplet-to-bubble transition and form microbubbles within the tumor. In this aspect and if a therapeutic agent is present in the nanoemulsion, the therapeutic agent will be efficiently and effectively administered to the tumor and will reduce tumor size and prevent tumor cell proliferation. In certain aspects, the methods described herein will kill tumors without damaging the surrounding normal cells and tissues or by minimally damaging the surrounding normal cells and tissues when compared to conventional treatments.

Also described herein are methods for reducing or preventing the onset or severity of tumor metastasis in a subject. In one aspect, the method comprises:
  (a) administering the nanoemulsion to the subject the nanoemulsion;
  (b) imaging the tumor metastases by $^{19}$F MRI and $^{1}$H MRI to identify the location of the nanoemulsion in the tumor metastases; and
  (c) exposing the tumor metastases to ultrasonic radiation.

For example, the nanoemulsion can be administered systemically to the subject. Once the nanoemulsion has had time to accumulate in the tumor metastases, the MRI such as $^{19}$F MRI can be used to locate the nanoemulsion. After the nanoemulsion has been located, the tumor metastases can be exposed ultrasonic radiation as described above. The exposure of the tumor metastases converts the nanoemulsion to microbubbles, which can ablate the tumor. Additionally, when the nanoemulsion contains a therapeutic agent, the agent is delivered to the tumor metastases when the nanoemulsion is exposed to ultrasonic radiation. The Examples provide exemplary procedures for using this method to identify the location of liver metastases.

Due to the stability of the nanoemulsions, it is possible to delay the release of the therapeutic agent by exposing the tumor to a first ultrasound having sufficient energy to release some of the therapeutic agent. Not wishing to be bound by theory, the microbubbles that do not release the therapeutic agent can re-condense in the tumor to the nanoemulsion when ultrasound is no longer applied. Thus, the nanoemulsion when present in the tumor behaves as a nanoimplant for future release of the therapeutic agent upon subsequent exposure to ultrasound.

The nanoemulsions described above can be administered to a subject using techniques known in the art. For example, pharmaceutical compositions can be prepared with the nanoemulsions. It will be appreciated that the actual preferred amounts of the nanoemulsion in a specified case will vary according to the specific nanoemulsions being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally). In the case of contacting cells with the droplets described herein, it is possible to contact the cells in vivo or ex vivo.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates. It is understood that any given particular aspect of the disclosed compositions and methods can be easily compared to the specific examples and embodiments disclosed herein based reagents discussed in the Examples. By performing such a comparison, the relative efficacy of each particular embodiment can be easily determined Particularly preferred compositions and methods are disclosed in the Examples herein, and it is understood that these compositions and methods, while not necessarily limiting, can be performed with any of the compositions and methods disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Paclitaxel Loaded PFCE Nanodroplets and Characterization Thereof a. Materials and Methods Block Copolymers.

Block copolymers poly(ethylene oxide)-co-poly(D,L-lactide) (PEG-PDLA), poly(ethylene oxide)-co-poly(L-lactide) (PEG-PLLA), and poly(ethylene oxide)-co-polycaprolactone (PEG-PCL) were from Polymer Source Inc. (Montreal, Quebec, Canada). The PEG-PDLA copolymer had a total molecular weight of 9,500 Da; the molecular weights of a hydrophilic PEG block and a hydrophobic PDLA block were 5,000 D and 4,500 Da respectively. The PEG-PLLA copolymer had a molecular weight of 9,700 Da, with corresponding block weights of 5,000 Da and 4,700 Da; the PEG-PCL copolymer had a total molecular weight of 4,600 Da, with corresponding block weights of 2,000 Da and 2,600 Da.

In some experiments, PEG-phospholipid compound, 1.2-distearoyl-sn-glycero-3-phosphoethanolamone-N-lmethoxy (polyethylene glycol)-2000 (PEG-PE) (Avanti Polar Lipids Inc., Alabaster, Ala.) and oligomeric PEG-containing fluorinated surfactant Zonyl FSO (Dupont product obtained through Sigma-Aldrich, St. Louis, Mo.) were admixed with PEG-PDLA in droplet shells. Introduction of PEG-PE allows simple conjugation of various ligands needed for active targeting of nanodroplets. It was found that in mixed copolymer/PEG-PE micelles or nanodroplets, a size signal of pure PEG-PE micelles disappeared from size distribution plots indicating that PEG-PE was incorporated into mixed copolymer/PEG-PE micelles or nanodroplet shells.

Zonyl FSO is a fluorine containing surfactant that promotes solubilization of highly hydrophobic perfluorocarbon compounds. Though being not essential for the formation of PFCE nanodroplets, Zonyl FSO was used in some PFCE formulations for consistency with other perfluorocarbon formulations used in the studies.

Preparation of Paclitaxel Loaded PFCE Nanodroplets.

Paclitaxel containing PEG-PDLA micellar solution was prepared by a solid dispersion technique. Typically, 50 mg of PEG-PDLA and 5 mg of paclitaxel were dissolved in 1 ml of tetrahydrofuran (THF). If desired, 10 mg PEG-PE was added. The THF was then evaporated under gentle nitrogen stream at 60° C. or evacuated in vacuum at room temperature. To produce paclitaxel containing micellar solution, the residual gel matrix was dissolved in 1 ml of phosphate buffered saline (PBS). Zonyl FSO solution in PBS was added in a desired concentration (usually 1.2% (vol.)) to this solution. Ten to fifty microliters of PFCE were introduced into 1 ml micellar solution and a mixture was emulsified by sonication in ice cold water (VCX500, Sonics and Materials, Inc., CT, USA) to obtain paclitaxel-loaded 1% to 5% (vol.) PFCE nanodroplets. PTX-loaded PFCE nanodroplets stabilized by PEG-PLLA or PEG-PCL shells.

Nanodroplet Introduction into Gels.

The nanodroplets were introduced into warm agarose solution in phosphate buffered saline (PBS) before gel formation. The liquid mixture was placed in a Samco transfer pipette (5-mm inner diameter, 0.3-mm wall thickness) (Fisher Scientific, Pittsburgh, Pa., USA) and cooled down to room temperature for gel formation.

Particle Size Distribution.

Size distribution of nanoparticles was measured by dynamic light scattering at a scattering angle of 165° using Delsa Nano S instrument (Beckman Coulter, Osaka, Japan) equipped with a 658-nm laser and a temperature controller. Particle size distribution was analyzed using the non-negative least squares (NNLS) method. The instrument allows measurement of particle sizes from 0.6 nm to 7 μm; microparticles larger than 7 μm cannot be measured accurately. Optical monitoring of the samples using an inverted microscope and hemacytometer (model 3200, Hauser Scientific, Horsham, Pa., USA) showed no microdroplets larger than 4 μm.

Sonication.

Unfocused 1-MHz ultrasound was generated by an Omnisound 3000 instrument (Accelerated Care Plus Inc, Sparks, Nev., USA) equipped with a 1-cm$^2$ piezoceramic crystal and 5-cm$^2$ probe head. Focused 1-MHz ultrasound was generated by a high intensity focused ultrasound (HIFU) transducer (H-101, Sonic Concepts, Bothell, Wash., USA) with an active diameter of 64 mm and focal length of 63 mm. The −3 dB lateral and axial pressure profiles were 1.2 and 10 mm respectively.

Monitoring Droplet-to-Bubble Transition.

The ultrasound-induced formation of microbubbles from nanodroplets was monitored at room temperature by ultrasound imaging, based on higher echogenicity of bubbles compared to droplets; a 7.5-MHz linear array scanner (Scanner 250, Pie Medical, Maastricht, The Netherlands) was used for ultrasound imaging, with 14 frames per second scan rate.

Cavitation Activity.

These measurements were performed with the samples placed in the Samco transfer pipettes. Cavitation activity was assessed by measuring harmonic, subharmonic, and broadband noise amplitudes in a portion of the scattered beam.

MRgHIFU Experiments.

All MRgHIFU experiments were performed in a Siemens TIM Trio 3T MRI scanner (Siemens AG, Erlangen, Germany). The MRgHIFU system (Image Guided Therapy, Bordeaux, France) uses a 256-element phased array transducer (1 MHz, 13 cm radius of curvature, 2×10 mm focal spot) with electronic steering capabilities in all three directions (+/−15 mm in x and y, +/−25 mm in z), as well as mechanical movement in the x-y plane. The temperatures were measured with the proton resonance frequency method using a 2D GRE sequence (TE=8 ms, TR=65 ms, flip angle=20°, 128×128 matrix, 5 slices). The maximum power deposition rate was found to be 0.0031 W/mm$^3$ in the phantom impregnated with nanodroplets. This value is consistent with a maximum power intensity of 80 W/cm$^2$ at the focal zone assuming an acoustic efficiency of 45%, an absorption value of 0.04 Np/cm/MHz and a beam size of 2.2×2.2×10 mm. In vivo, the maximum power deposition rate was found to be 0.001 W/mm$^3$. This value is consistent with a maximum power intensity of 54 W/cm$^2$ at the focal zone assuming an acoustic efficiency of 45%, an absorption value of 0.03 Np/cm/MHz and a beam size of 2.2×2.2×10 mm.

$^{19}$F MR Imaging.

To perform $^{19}$F MR spectroscopy ($^{19}$F MRS) or imaging ($^{19}$F MRI) on the 3T human MRI system, a transmit/receive $^{19}$F/$^1$H dual-tune volume RF coil with hardware interface consisting of a quadrature transmit/receive (Tx/Rx) switch, coil-selector, and pre-amplifier was constructed in house by EKJ. The coil had a 3.8 cm inner diameter and a 7.6 cm length. The pre-amplifier had an operational bandwidth of 3-200 MHz. Tx/Rx switching was accomplished using a quarter-wave coaxial cable and PIN diode, to which the DC bias voltage was supplied from the imaging system. The isolation between Tx and Rx ports was −40 dB during the RF transmission. The Tx/Rx switching interface is equipped with a coil selection switch for $^{19}$F/$^1$H MRI, because the λ/4 length of two nuclei is similar to within 5%. In the $^{19}$F MRS measurements of excised organs, surface coil designed for the rabbit eye experiments was used.

Cells.

Human breast cancer MDA MB231 cells and pancreatic cancer MiaPaCa-2 cells were obtained from American Type Culture Collection (Manassas, Va.). Cells were cultured in RPMI-1640 medium supplemented with 10% heat-inactivated fetal bovine serum (FBS) (Gibco, Grand Island, N.Y.) at 37° C. in humidified air containing 5% $CO_2$. Pancreatic cancer MiaPaCa-2 cells were transfected with red fluorescence protein (RFP). Pancreatic cancer cells were maintained in DMEM supplemented with 10% FBS.

Animal Procedures.

Four to six weeks old nu/nu mice were obtained from Charles River Laboratories (Wilmington, Mass.). Animals were housed in accordance with the Guide for the Care and Use of Laboratory Animals as adopted by the National Institutes of Health. All experiments were performed in accordance with the guidelines of the Institutional Animal Care and Use Committee of the University of Utah (Protocol 08-01001). For breast cancer inoculation, cells were suspended in serum-free RPMI-1640 medium and inoculated subcutaneously to the flanks of unanaesthetized mice (1×10$^6$ cells/100 μL/mouse). For the implantation of orthotopic pancreatic cancer tumors, 1.5×10$^6$ RFP expressing MiaPaCa-2 cells suspended in DMEM media were surgically injected into the tail of the pancreas.

Measuring Nanodroplet Pharmacokinetics.

These experiments were performed using 3 month old Swiss Webster white mice obtained from Charles River Laboratories (Wilmington, Mass.) Animals were housed in accordance with the Guide for the Care and Use of Laboratory Animals as adopted by the National Institutes of Health. Each animal was systemically injected with 300 μl of 5% PFCE nanodroplet formulation. At chosen time points (30 min; 2 h; 6 h; 24 h) animals were anesthetized, blood was collected by cardiac puncture, then animals were sacrificed, organs (the liver, spleen, lung, and heart) were excised, weighted and kept refrigerated until $^{19}$F MRS measurements that were performed the same day. Experiments were run in triplicates. Two types of nanodroplet shells formed by either PEG-PDLA or PEG-PCL were tested; copolymer concentration was 1% (wt.); shell-forming copolymers were mixed with 0.25% (wt.) PEG-PE; Zonyl FSO concentration was 0.6% (vol.).

Ultrasound Imaging.

Ultrasound imaging was performed using Acuson Sequoia 512 linear transducer (Siemens, Mountain View, Calif.).

b. Results

Physical and Acoustic Properties of PFCE Nanoemulsions

Size Distribution.

The data for empty and PTX-loaded PEG-PDLA micelles and PEG-PDLA stabilized nanodroplets are presented in FIGS. 1A-D. The size of both, micelles and nanodroplets increased after PTX loading. Size distributions for empty and PTX-loaded micelles are presented in FIGS. 1A and 1B respectively.

Typically, at a 1% (vol.) PFCE concentration in a 5% PEG-PDLA micellar solution, a bimodal distribution of nanodroplet sizes was observed corresponding to a mixture of micelles (81.6±14.7 nm) and nanodroplets (275±50 nm), as illustrated in FIG. 1C. The micelle/droplet ratio decreased with increasing PFCE concentration; micelles disappeared at PFCE concentration of 5% (FIG. 1D) indicating that all block copolymer was transferred from micelles onto droplet surfaces. Typically, after PFCE emulsification in the PTX-loaded micellar solutions, the size of droplets increased from 275±50 nm for empty droplets to ca. 300-500 nm for PTX-loaded droplets, while the size of micelles dropped to values corresponding to empty micelles indicating that PTX was transferred from micelles to nanodroplets. The size of PTX-loaded PFCE nanodroplets presented in this work was consistently smaller than that of the PTX-loaded perfluoropentane (PFP) nanodroplets. This reduction in size is particularly beneficial for drug delivery applications.

Optical microscopy of PFCE formulations indicated presence of a small population (fraction of percent) of droplets of micron-range sizes (up to 3 μm) that avoided measurement by dynamic light scattering due to precipitation to the bottom of the cuvette during the measurement process.

Echogenic Properties.

Figure 2:
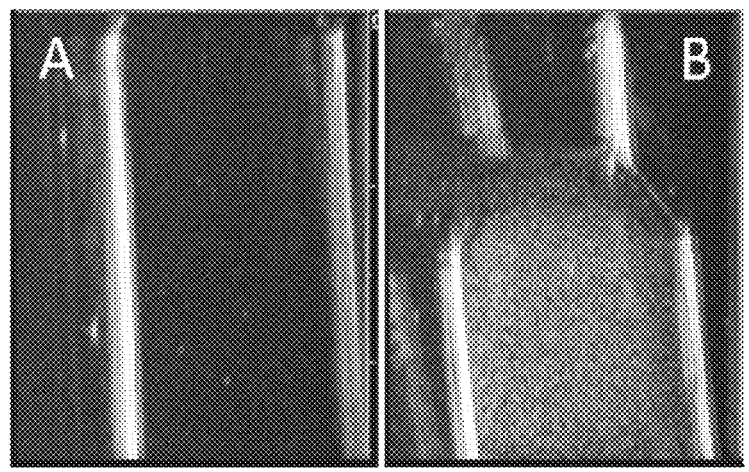
FIG. 2 shows the ultrasound images of (A) pure agarose gel in a test tube and (B) PFCE nanodroplet loaded agarose gel; a 1.2% agarose solution in PBS was mixed with an equal volume of 2% PFCE nanodroplet emulsion at 50° C. to produce 1% (vol.) nanodroplet concentration in the gel. The mixture was cooled to room temperature to solidify. Note higher echogenicity of the nanodroplet loaded gel. This effect did not depend on the type of the copolymer used to form droplet shell.

Due to large differences in acoustic impedances between perfluorocarbons and water, PFCE nanodroplets generate relatively strong ultrasound contrast (FIG. 2).

Droplet-to-Bubble Transition.

Figure 3:
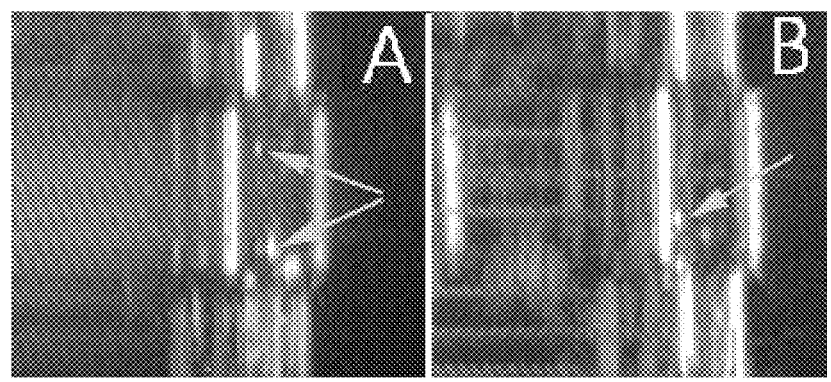
FIG. 3 shows droplet-to-bubble transition in 1% PFCE/ 0.25% PEG-PLLA nanoemulsions is manifested by generation of bright specks in ultrasound images (indicated by arrows). (A) continuous wave 1-MHz ultrasound; (B) pulsed 1-MHz ultrasound, pulse length 3 ms, 20% duty cycle. Similar results were obtained for PEG-PDLA, PEG-PCL, and copolymer mixture stabilized nanoemulsions.

Despite high boiling temperature of 146° C., nanodroplets converted into microbubbles under the action of therapeutic ultrasound, as manifested in FIG. 3 by the formation of bright specks in the ultrasound images of PFCE nanoemulsions sonicated with continuous wave (CW) (FIG. 3A) or pulsed (FIG. 3B) ultrasound. The bubbles formed under ultrasound were moving upward; however upon turning ultrasound off, they reversed direction of motion and were returning back to the bottom of the test tube thus indicating that droplet-to-bubble transition was reversible. The observation that droplet-to-bubble transition proceeded under pulsed ultrasound (FIG. 3B) suggested that the mechanical component of ultrasound played predominant role in inducing droplet vaporization because sample heating under pulsed ultrasound did not exceed two-three degrees Celsius in our experimental setting, which could be considered negligible for purely thermal vaporization of PFCE. Ultrasound-induced droplet-to-bubble transition is called acoustic droplet vaporization (ADV). ADV thresholds were slightly higher for PFCE nanodroplets compared to PFP nanodroplets stabilized by the same copolymer (Table 1).

TABLE 1

Comparisons of ADV thresholds for the 1% PFP and 1% PFCE nanodroplets stabilized by PEG-PLLA copolymer. Peak rarefactional pressures are presented.

| | Sample | | | |
|---|---|---|---|---|
| | 1% PFP/0.25% PEG-PLLA | | 1% PFCE/0.25% PEG-PLLA | |
| Duty cycle | 20% | 100% | 20% | 100% |
| Threshold (Mpa) | 0.20~0.23 | 0.14~0.16 | 0.34~0.41 | 0.20~0.23 |

Bubble Cavitation.

Figure 4:
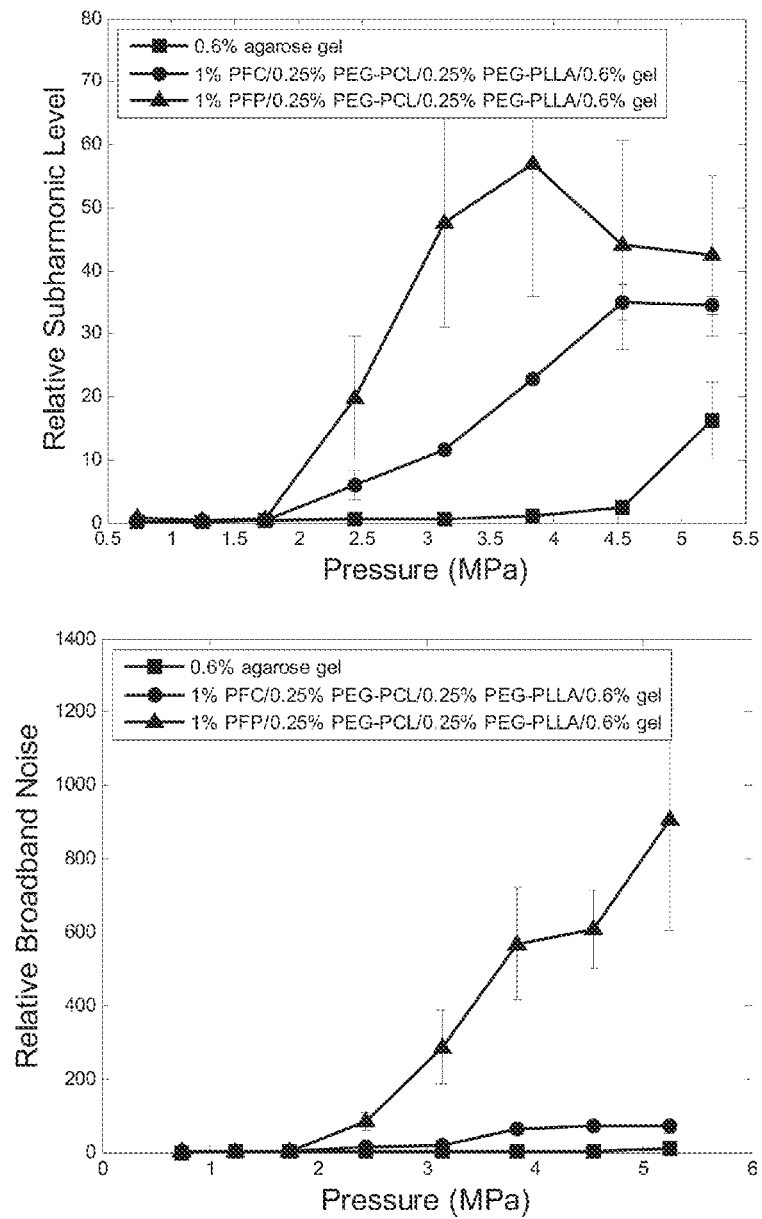
FIG. 4 shows the relative subharmonic (top) and broadband noise (bottom) levels generated under the action of 1-MHz focused ultrasound (HIFU) at room temperature by PFP and PFCE nanodroplets inserted into the 0.6% agarose gel. Nanodroplets were stabilized by a mixture of 0.25% PEG-PLLA/ 0.25% PEG-PCL copolymer. Triangles—PFP droplets; circles—PFCE droplets; squares—pure agarose gel.

Cavitation effects of the bubbles formed via ADV were explored for unfocused ultrasound and HIFU at a frequency of 1 MHz. The appearance and amplitudes of harmonic frequencies and broadband noise were monitored in the Fast Fourier Transform emission spectra. The results shown in FIG. 4 indicate that bubbles formed by the ADV of PFCE nanodroplets oscillated under the action of ultrasound, similar to the effects observed for PFP nanoemulsions. Though oscillation amplitudes were somewhat smaller for PFCE than for PFP, PFCE bubbles clearly underwent stable cavitation both in liquid emulsions and gel matrices. Larger differences between PFP and PFCE bubbles were observed for broadband noise intensities indicating that PFCE bubbles were less susceptible to inertial cavitation.

PFCE bubbles stabilized with PEG-PDLA shells generated higher subharmonic and broadband noise amplitudes than those stabilized with PEG-PLLA or PEG-PCL (data not shown), presumably due to amorphous PDLA blocks forming softer nanodroplet shells in comparison with those formed by crystalline PLLA or PCL blocks.

Under lower ultrasound pressures generated by an unfocused Omnisound 3000 transducer, cavitation amplitudes of PFCE bubbles inserted in a gel matrix were relatively small while inertial cavitation was not manifested (data not shown). This result directed the choice of HIFU transducer for pilot tumor therapy experiments using a breast cancer model. Strong therapeutic effect observed in this pilot study (see below) encouraged testing lower energy unfocused ultrasound in subsequent larger scale experiments with a pancreatic cancer model.

MRI Thermometry of a PFCE Droplet Loaded Gel Phantom Under Focused Ultrasound (FUS) Irradiation.

These experiments were performed in agarose gel phantoms that were either "empty" or loaded with PFCE nanodroplets. The results of temperature measurements by the MRI thermometry are shown in FIGS. 5A and 5B. Temperature rise was much faster and the temperature achieved under FUS irradiation was much higher for the nanodroplet-containing gel in comparison to the empty gel. The data indicate that the acceleration of FUS-induced heating was associated with ultrasound absorption by PFCE nanodroplets.

In Vivo MRI Thermometry and Therapeutic Properties of Systemically Injected PFCE Nanodroplets in Pancreatic Tumor Bearing Mice Subjected to FUS Irradiation.

Figure 7:
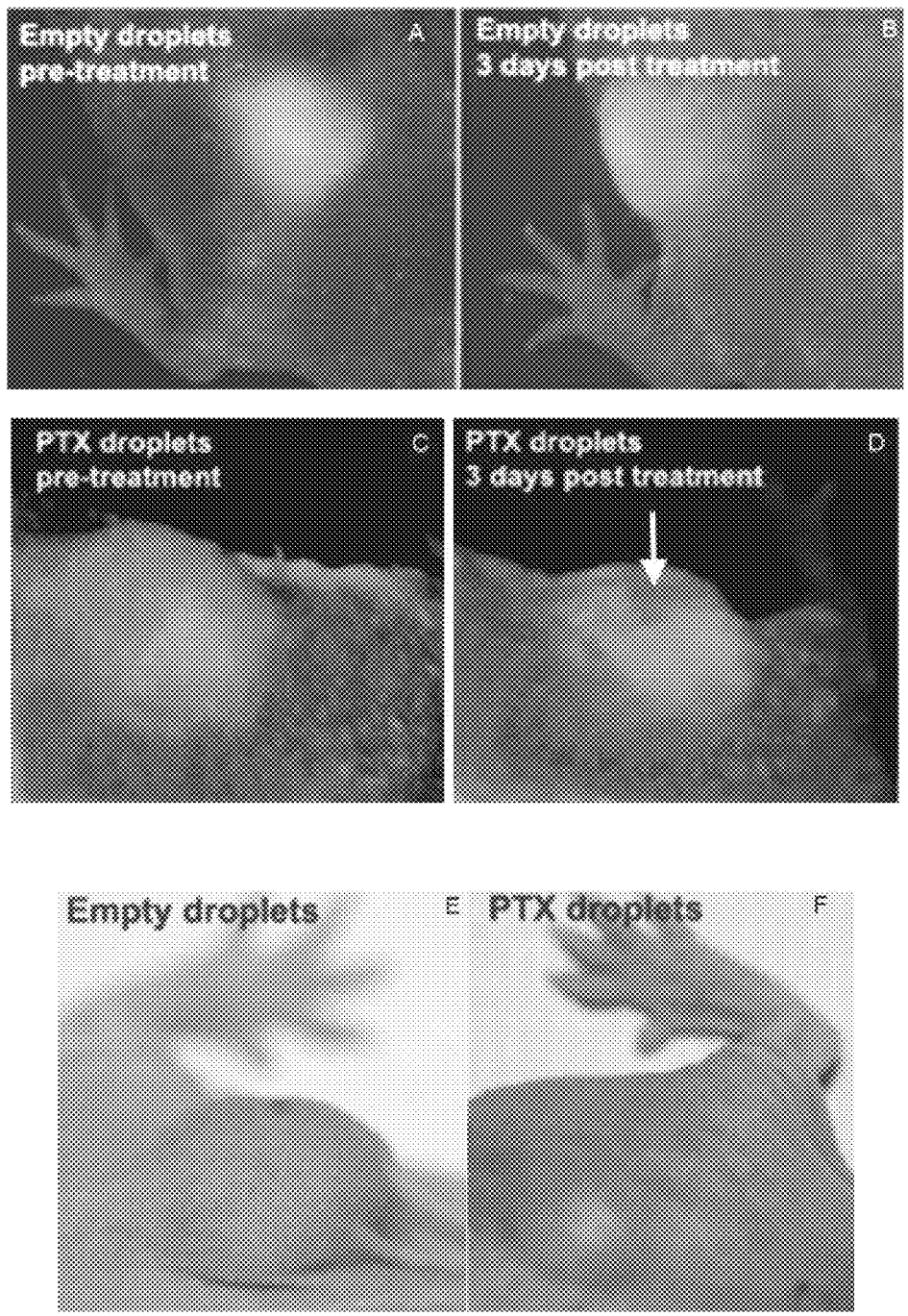
FIG. 7 shows intravital fluorescence images of red fluorescence protein transfected subcutaneous pancreatic tumors before and after FUS treatment (A-D). Mice were injected with empty droplets (A, B) or PTX-loaded droplets (C, D). Fluorescence images of initial tumors are shown in panels A and C; images recorded three days after treatment are shown in panels B and D. Photographs of the tumors were taken 12 days after the treatment for empty droplets (E) and PTX-loaded droplets (F). Conditions of FUS treatment are presented in caption to FIG. 6B. Mice were systemically injected with empty or PTX-loaded 1% PFCE/5% PEG-PDLA nanodroplets six hours before FUS treatment; DOX dose was 40 mg/kg.

Experimental setup for the in vivo FUS application is schematically presented in FIG. 6A. Kinetics of temperature rise for the subcutaneous pancreatic tumors systemically injected with the empty (solid line) or paclitaxel loaded nanodroplets (dashed line) are presented in FIG. 6B. Ultrasound beam was steered for 50 s in a circle of 4-mm diameter (8 "points", 200 ms/point, 30 circles per treatment resulting in a 6-s sonication of each "point"). Maximum temperature measured by the MRI thermometry in coronal slices was slightly higher for a mouse injected with empty nanodroplets, which could be related to different concentration of tumor-accumulated nanodroplets; however it could be also an experimental problem associated with the 1-mm separation of measured coronal slices (maximal attained temperature could be located between the two slice)s. Despite lower measured maximal temperature, the therapeutic effect was much stronger for drug-loaded nanodroplets (FIG. 7). Initial tumor sizes were close for both mice (the tumor treated with PTX-loaded nanodroplets being initially slightly larger than that treated with empty nanodroplets, compare fluorescence images of FIGS. 7A and 7C). Note that only viable tumor cells generate Red Fluorescence Protein and therefore produce fluorescence.

No trace of cell death was observed in fluorescence images of a FUS-treated mouse injected with empty nanodroplets (FIG. 7A, B). In contrast, cell death was clearly manifested in fluorescence images of a FUS-treated mouse injected with PTX-loaded nanodroplets (FIG. 7 C, D). The area of killed cells (approximately 4 mm diameter) corresponded to the FUS-treated area. FIG. 7D shows that the PTX action on the tumor cell killing was substantially enhanced by ultrasound. "Cavernous" appearance of the tumor in FIG. 7D is an optical effect associated with dead cells losing fluorescence; real tumor did not have any depression (FIG. 7 F). Tumor photographs taken twelve days after treatment (FIG. 7 E, F) indicate that tumor growth was effectively delayed after only one tumor treatment with PTX-loaded nanoemulsions and ultrasound; note that only a fraction of the total tumor volume was treated by ultrasound. Larger scale experiments on pancreatic cancer chemotherapy with PTX-loaded nanoemulsions and ultrasound using orthotopic pancreatic cancer model are presented below.

Figure 8:
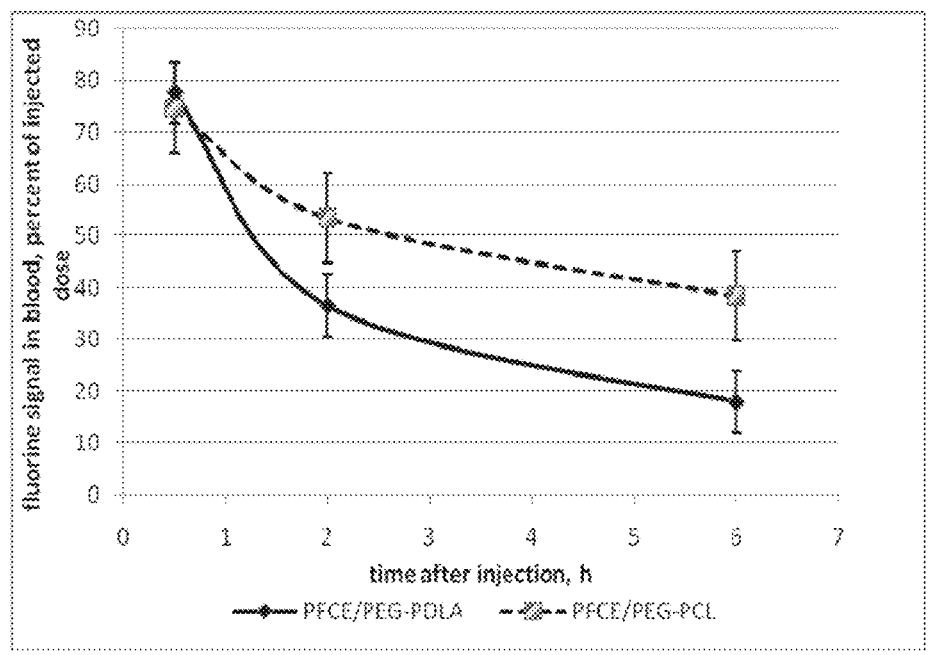
FIG. 8 shows nanodroplet pharmacokinetics measured with $^{19}$F MRS(N=3; mean value plus/minus standard deviation is presented).

Therapeutic and Imaging Properties of PFCE Nanoemulsions
PFCE Nanodroplets are Long Circulating Fluorine MR spectroscopy ($^{19}$F MRS) was used for quantitatively monitoring nanodroplet pharmacokinetics and biodistribution in healthy white Swiss Webster mice as described in Materials and Methods section. The pharmacokinetic curves are shown in FIG. 8 for the two types of nanodroplet stabilizing copolymers. The curves indicate that both types of nanodroplets were long circulating. About seventy percent of the injected dose remained in circulation thirty minutes after the systemic injection; forty to fifty percent were still circulating two hours after the injection; for PEG-PCL stabilized nanodroplets, forty percent of the injected dose remained in circulation six hours after injection; even twenty four hours after injection, about ten percent of the injection dose was still found in the blood while about eighty percent was fond in the liver (these data are not presented in the graphs because only one mouse for each formulation was used at the 24-hour time point). Nanodroplets were taken up mainly by the liver and spleen; the uptake by other organs was below the $^{19}$F MRS sensitivity. On the per organ basis, the major nanodroplet uptake was observed for the liver, while on the per gram basis, for up to 6 hours after the injection, the uptake was significantly higher for the spleen; the uptakes by the liver and spleen were gradually equalized at later stages.

Nanodroplet Biodistribution in Tumor Bearing Mice
Ultrasonography.

Due to the echogenic properties of PFCE nanodroplets, their tumor accumulation and biodistribution can be monitored by ultrasonography. Ultrasound imaging showed that after systemic injection, PFCE intratumoral distribution in the orthotopic human pancreatic MiaPaCa-2 tumors surgically inoculated in nude mice was highly non-uniform, as was reported earlier for PFP nanodroplets. Note that pancreatic tumors are very poorly vascularized, with functional blood vessels localized predominantly in the tumor rim.

Figure 9:
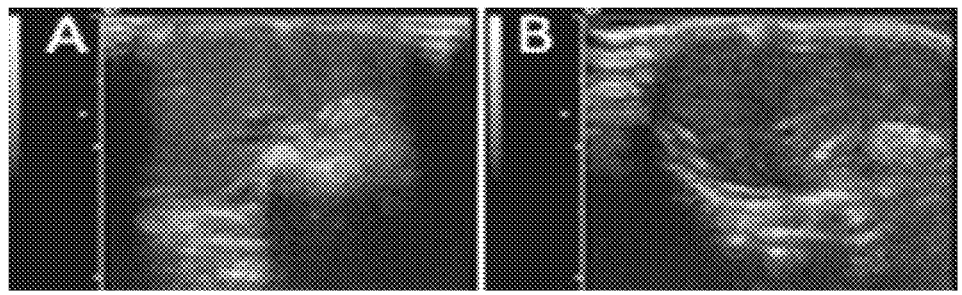
FIG. 9 shows ultrasound images of the liver. (A) Mouse was injected with 0.25% PEG-PCL stabilized nanodroplets; (B) mouse was injected with nanodroplets stabilized with a surfactant mixture comprising 5% PEG-PDLA, 1% PEG-PE, and 1.2% Zonyl FSO (tumor image for this mouse is shown in FIG. 9B). Note significant differences in the liver echogenicity between panels 10A and 10B (50 arb.u. vs 25 arb.u. as measured by the NIH ImageJ software), which indicates lower liver uptake of nanodroplets stabilized with a surfactant mixture.

Similar to the tumor, nanodroplet uptake by the liver causes an increase in liver echogenicity. The degree of liver enhancement depended on the composition of the nanodroplet shell; significant differences in the liver uptake were observed between 0.25% PEG-PCL stabilized nanodroplets (FIG. 9A) and those stabilized with a surfactant mixture comprising 5% PEG-PDLA, 1% PEG-PE, and 1.2% Zonyl FSO (FIG. 9B). These data indicate that the liver uptake of nanodroplets can be modulated by optimizing composition of nanodroplet shells.

Fluorine MRI of PFCE Nanodroplets after Systemic Injections.

PFCE has twenty equivalent fluorine nuclei, which provides for a sharp fluorine peak in the MR spectra and allows $^{19}$F MR imaging of PFCE nandroplets in vitro and in vivo. In the pilot experiments described below, $^{19}$F MR images of the orthotopic pancreatic cancer bearing mouse are presented.

Figure 10:
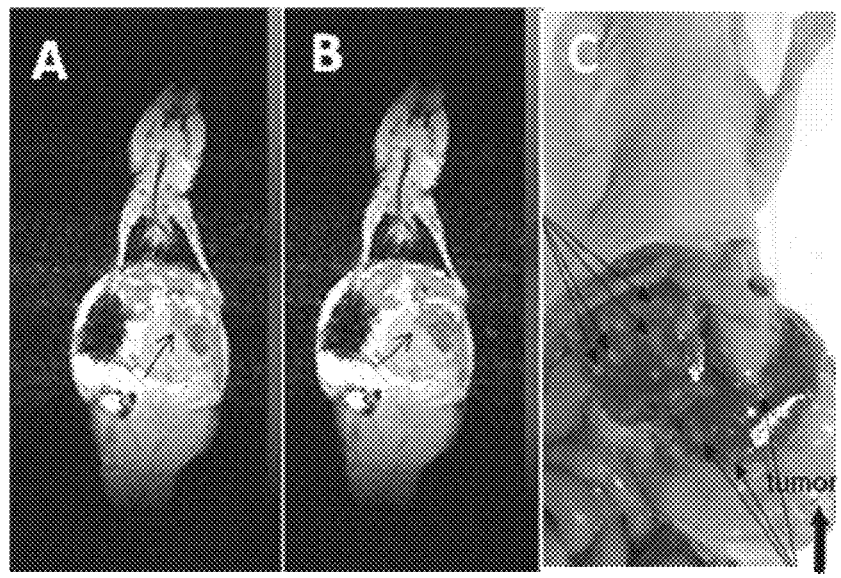
FIG. 10 shows (A) and (B) two coronal slices in the $^{19}$F MR images superimposed on the low resolution proton anatomic images of a pancreatic tumor bearing mouse. A 2% PFCE nanoemulsion stabilized with PEG-PCL copolymer was systemically injected every two hours, 200 μl each. Four injections were given, for a total of the PFCE dose of 2 mmol/kg. Images were recorded an hour after the last nanodroplet injection (seven hours after the start). Imaging parameters: Proton imaging: GRE (Gradient Recalled Echo) pulse sequence, resolution 1×1×3 mm, TR/TE=400/4.24, matrix 128×128, average 12; the $^{19}$F imaging: GRE pulse sequence, resolution 2×2×3 mm, TR/TE=400/4.24, matrix 64×64, average 32. (C) Multiple liver metastases (arrows) are revealed at the necropsy of the mouse (indicated by long thing arrows). Transparent large tumor is indicated by a thick arrow. Organs could be displaced at necropsy.

In the experiment presented in FIG. 10, mouse was injected every two hours with 200 μl of 2% PFCE/0.5% PEG-PCL nanodroplets; a total of four injections were given, for an injected PFCE dose of 16 μl or 2 mmol/kg. The $^{19}$F MR images superimposed on the low resolution proton images are shown in FIG. 10A,B for two coronal slices. Fluorine atom locations were clearly observed, with signal-to-noise ratio of 24. The fluorine was located in the liver and its distribution was clearly speckled. Fluorine signal was also seen in the upper locus of the tumor (indicated by arrows); however the interpretation of this signal is ambiguous because it could come from the lower end of the liver lobe fused with the tumor. Necropsy images presented in FIG. 10C show a large tumor with multiple liver metastases, which is typical for 40% of orthotopically inoculated pancreatic tumors. These data show the feasibility of using $^{19}$F MRI for intravital monitoring of nanodroplet location. Further experiments are required to identify the origin of the voxels with the accumulated nanodroplets in order to discern signals coming from the liver tissue, liver metastases, and tumor.

Measurement of nanodroplet concentration in tumor tissue by $^{19}$F MRI is complicated by a strong dependence of the fluorine nucleus relaxation time T2 on the local oxygen concentration, i.e. tumor oxygenation. Due to this effect, hypoxic areas of tumors produce very low, if any MRI signal. Therefore fluorine signals visualized in the tumor tissue depend not only on the concentration of fluorine nuclei but also on oxygen concentration, i.e. on the geometry of tumor vascularization. This makes fluorine MRI a poor quantitative indicator of the intratumoral uptake of nanodroplets, especially for poorly vascularized tumors such as pancreatic cancer. For such tumors, information provided by $^{19}$F MR images may suffer from the underestimation of the intratumoral nanodroplet uptake and distribution. This problem is not imminent to $^{19}$F MR images of highly vascularized organs such as the liver, spleen, heart, or lung.

Pilot Experiment on the Ultrasound-Mediated Chemotherapy of a Breast Cancer Tumor Xenograft Using Paclitaxel-Loaded PFCE Nanoemulsion Combined with 1-MHz Focused Therapeutic Ultrasound.

In these experiments, breast cancer MDA MB231 tumor was treated by four systemic injections of paclitaxel loaded 1% PFCE/0.25% PEG-PCL nanoemulsion and focused 1-MHz CW ultrasound; treatment was given twice weekly for two weeks as described in the Methods section. Paclitaxel dose was 40 mg/kg. Ultrasound pressure at the first treatment was 2.74 MPa. It was reduced to 2.0 MPa in subsequent treatments due to some skin burn that required treatment with antibiotic ointment.

Figure 11:
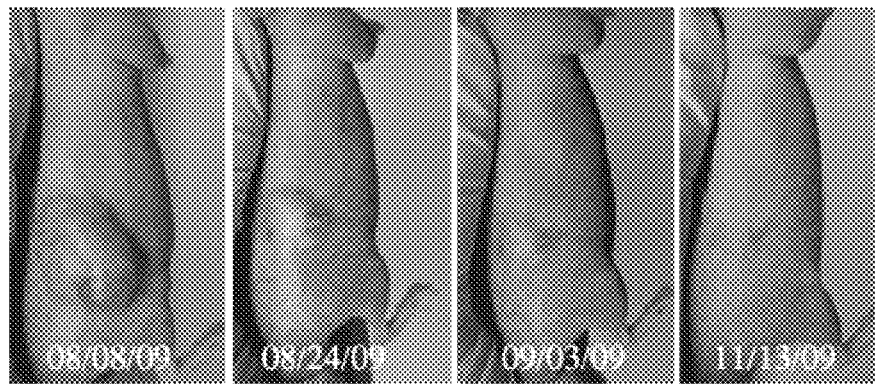
FIG. 11 shows the dramatic regression of a breast cancer MDA MB231 tumor treated by four systemic injections of paclitaxel loaded 1% PFCE/0.25% PEG-PCL nanoemulsion and focused 1-MHz CW ultrasound applied for 60 s as described in Methods section. Paclitaxel dose was 40 mg/kg. The tumor of an anesthetized mouse was inserted into a water tank and sonicated by ultrasound generated by the HIFU transducer. During the first treatment, sonication was performed in water maintained at room temperature, which caused significantly extended period of anesthesia; peak rarefactional pressure was 2.74 MPa; this caused some skin burn that were treated by antibiotic; for subsequent treatments, the pressure was reduced to 2.0 MPa and water temperature was maintained at 33° C.

Complete tumor regression was observed as shown in FIG. 11. No tumor relapse occurred during a five-month monitoring period. Dramatic therapeutic effect observed in this study encouraged testing lower ultrasound energies generated by unfocused ultrasound transducer in subsequent larger scale experiments using orthotopic pancreatic cancer model. The results of this study are presented below.

Ultrasound-Mediated Chemotherapy of the Orthotopic Pancreatic Cancer Xenografts Using Paclitaxel-Loaded PFCE Nanoemulsion Combined with 1-MHz Unfocused Therapeutic Ultrasound.

Figure 12:
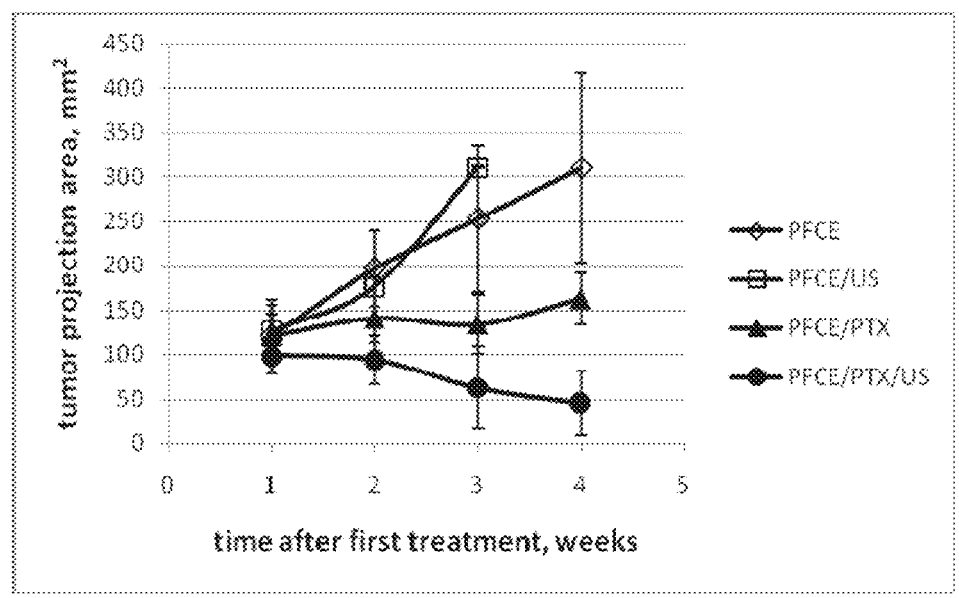
FIG. 12 shows tumor growth/regression curves for pancreatic cancer bearing mice treated with either empty (open symbols) or PTX-loaded (closed symbols) 1% PFCE/5% PEG-PDLA nanodroplets. PTX dose was 40 mg/kg. N=4 (empty symbols); N=5 (filled symbols).

The results obtained in the experiments presented in FIG. 12 are qualitatively similar to those obtained earlier with PFP nanodroplets. No therapeutic effect was observed for empty nanodroplets with or without ultrasound (empty symbols in FIG. 12). Paclitaxel loaded nanodroplets caused disease stabilization (closed triangles) while combining paclitaxel loaded nanodroplets with tumor sonication resulted in tumor regression (closed circles). All animals treated with empty droplets (N=4 in each group) developed metastases and ascites while no metastases or ascites was observed in animals treated with drug-loaded nanodroplets with or without ultrasound (N=5). These data indicate unambiguously that the therapeutic effect was caused by drug and not by ultrasound. The action of the micellar or nanodroplet encapsulated drug was enhanced by ultrasound, as was also indicated by the data presented in FIG. 7; the difference between the sonicated and non-sonicated drug loaded groups was statistically significant in a two-tail equal variance Student's test (P<.0.05).

II. Doxorubicin Loaded PFCE Nanodroplets and Characterization Thereof a. Materials and Methods Preparation of Empty PEG-PLLA Solution.

Solution of 2.5% (w/v) PEG-PLLA (5000 Da molecular weight of the PEG block and 4700 Da of the PLLA block; purchased from Polymer Source, Quebec, Canada) was prepared by first dissolving the polymer in Tetrahydrafuran (THF). Filtered water was then added to the polymer in THF solution to get an aqueous solution of 0.5% (w/v) PEG-PLLA. This solution was transferred to a membrane tube (SpectraPor, Spectrum Laboratories Inc, Rancho Dominguez, Calif.) with a molecular cutoff of 3500 Da. The organic solvent was removed by dialysis against water. The change of external liquid was repeated three times, with the final dialysis against phosphate buffered saline solution (PBS). The final copolymer concentration was 0.5% (w/v) PEG-PLLA solution. From here on, all copolymer concentrations are reported in w/v percentages. After preparation, the solution was refrigerated until use. The formulation was later diluted with PBS to obtain desired copolymer concentrations.

Preparation of Empty and DOX Loaded PEG-PCL Solution.

Empty PEG-PCL micelles was prepared similar to 0.5% PEG-PLLA solution discussed in the previous section. Commercial doxorubicin (Sigma aldrich, St. Louis, Mo.) is marketed as hydrochloride salt in order to increase its aqueous solubility. However for efficient incorporation of the drug into the hydrophobic micelle cores, the drug needs to be lipophilic. The drug can be made lipophilic by removing the quaternization from amino group. This is achieved by incubating DOX with triethylene amine (TEA), which results in amino group deprotonation. The 1% (v/v) TEA solution in dimethyl sulfoxide (DMSO) was stirred overnight with 20 mg/ml DOX to produce 2:1 TEA/DOX molar ratio. Copolymer poly(ethylene glycol)-co-polycaprolactone (PEG, 2k-PCL, 2.6 k) was first dissolved in the tetrahydrofuran (THF) to the concentration of 5% (w/v), and then mixed with the prepared DOX solution. This was followed by addition of filtered 1× phosphate buffered saline (PBS) solution to get a final copolymer concentration of 1% (w/v) and DOX concentration of 65 µg/mL. DMSO in this solution was less than 1.6% (v/v) concentration. This mixture was sonicated to accelerate mixing. The organic solvent in the mixture was removed by evaporation in a nitrogen stream. The micellar solution (volume of 4 mL) formed, was ultracentrifuged at 4,000 g for 60 min through a 30000 Da cutoff membrane to remove free DOX and excess of TEA dissolved in PBS from the DOX encapsulated in micelles. The residual copolymer solution volume inside the membrane compartment was 225 µl. It was resuspended in 3.775 µl of empty 0.5% micellar solution of PEG-PCL in PBS to produce final copolymer concentration of 1.4%.

Preparation of Emulsion.

Using a cooled pipette tip, 2 ml of either empty copolymer solution or DOX incorporated copolymer solution was placed in a cooled container and 40 µL of either perfluoro-15-crown-5-ether ($C_{12}F_{24}O_6$, PFCE) (Sigma Aldrich, USA) or perfluoropentane (PFP) was added to obtain empty/DOX loaded 2% (vol/vol) PFCE/1.4% copolymer composition and 2% PFP/1.4% copolymer composition. The PFCE or PFP aqueous emulsions were prepared by sonicating the mixture at 20 kHz using an ultrasound probe (cup-horn installation, Sonics, Newtown, Conn.) inserted in ice cold water. Size distribution and morphology of surfactants and droplets. Size distribution of PEG-PLLA and PEG-PCL micelles; and PEG-PLLA stabilized PFP and PFCE emulsions were analyzed using dynamic light scattering (Delsa Nano S, Beckman Coulter, BREA, CA), which produced reliable size measurements in the range from 10 nm to 3 µm. Scattered light intensity measurements were analyzed using autocorrelation method and the size distribution curves were obtained by fitting the measured autocorrelation functions using non-linear least squares method. Droplets larger than 1 µm precipitate from the suspension and thus cannot be reliably measured using light scattering. Thus the size of larger droplets was characterized microscopically, using a hemocytometer. Morphology of PEG-PLLA and PEG-PCL structures formed in the solution was characterized by transmission electron microscopy (Tecnai 12, FEI, Hillsboro, Oreg.). A small volume (10 µL) of the copolymer solution was placed on a 200 mesh carbon grid coated with Formvar carbon film (200C-FC, Electron Microscopy Sciences, Hatfield, Pa.). The solution was allowed to dry for 15 minutes, and the excess solution was absorbed with a filter paper. 10 µL of phosphotungstic acid was added on the grid to stain the micellar structures. Staining time was for 30 seconds after which the excess solution was removed using a filter paper. The grid was then placed in the vacuum chamber of the TEM, subjected to an accelerating voltage of 120 kV, and imaged. Morphology of droplet residues from 0.25% PEG-PLLA 2% PFP emulsion solution was also visualized using TEM by employing this method. The following sections reports and discusses the size distribution and morphology of surfactant and droplet solution.

Characterization of Empty and DOX Loaded PEG-PCL Solution.

Size distributions of 1.0% PEG-PCL empty surfactant solution and DOX-loaded 1.4% PEG-PCL solution measured by dynamic light scattering (DLS). Major distribution peaks were slightly larger for DOX-loaded than empty micellar solutions. Transmission electron microscopy (TEM) image of diluted DOX loaded 0.0025% PEG-PCL solution, showed the presence of spherical micelles over a size range of 5-20 nm, which corresponded to the size distribution indicated by the DLS method.

Characterization of PEG-PLLA Stabilized PFCE and PFP Droplets.

Similarly, the droplet size distribution in 1.4% PEG-PCL stabilized 1% PFCE and 1% PFP solutions measured by DLS shows presence of two populations with peaks around 90 and 320 nm for perfluoro-15-crown-5-ether droplets, and larger size distributions with peaks at 160 and 720 nm for perfluoropentane droplets. The emulsion samples were also imaged by optical microscopy, where few larger droplets (>1 µm) were observed for both PFCE and PFP emulsion.

Determination of Drug Loading Content.

To determine the DOX loading efficiency for 1.4% PEG-PCL copolymer solution and 1.4% PEG-PCL/2% PFCE/PFP droplets, UV-vis absorbance spectra of the samples were recorded using a microplate reader (SpectraMax M2$^e$, Molecular Devices, Sunnyvale, Calif.) in the wavelength range of 400 to 550 nm. The absorbance of the samples was quantified based on the control curve that gave linear dependence for DOX optical density on concentration. For measuring DOX incorporation into nanodroplets, the droplets were removed by centrifugation and the residual DOX concentration in copolymer was measured by optical spectroscopy. The difference in spectra peaks between the initial micellar solution and the supernatant after droplet centrifugation indicated the amount of DOX loaded onto droplets.

UV-Vis spectra of aqueous solutions of different concentrations of DOX in PBS, DOX loaded copolymer solution, supernatant after centrifuging PFCE and PFP droplets were obtained. The peak absorbance at 490 nm from the corresponding baseline was measured. The standard curve of peak absorbance was plotted against concentration of DOX. A linear relation between the concentration of DOX and peak absorbance values was observed. The amount of initial DOX in 1% PEG-PCL solution before filtration was 65 µg/mL. The amount of DOX in final resuspended 1.4% PEG-PCL copolymer solution was 20 µg/mL DOX. The amount of free DOX lost in the filtrate was also measured and was found to be 39 µg/mL. Some amount of DOX was lost during centrifuging due to DOX sticking to the membrane. DOX loading (final/initial DOX concentration (%)) was found to be 32.5%, whereas the DOX loading ratio (DLR, drug weight/polymer weight) was found to be 0.2% (w/w). A low initial DOX concentration was initially used in order to avoid well known high concentration quenching of DOX fluorescence in cellular experiments. After incorporation of perfluorocarbon droplets, the fraction of DOX loaded on droplets was calculated as DOX concentration in droplets/DOX concentration in PEG-PCL solution.

The DOX loading in PFCE and PFP droplets was 15%. Final formulations of 1.4% PEG-PCL-stabilized 1% PFCE or 1% PFP droplet solution contained DOX concentration of 20 µg/mL that partitioned between droplets and micellar structures in the ratio of 15% to 85% respectively.

Figure 13:
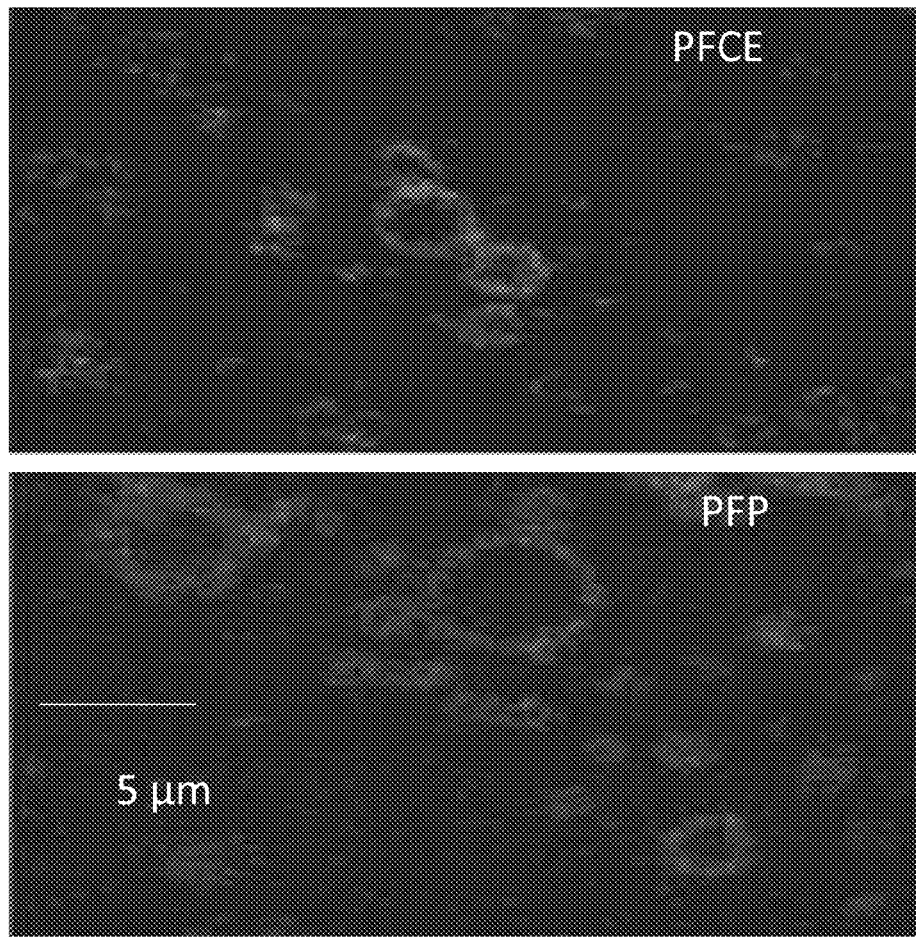
FIG. 13 shows confocal fluorescent images of DOX loaded PFCE (top) and PFP (bottom) droplets suspended in PBS. Nanosized droplets cannot be easily visualized, but the micron sized droplets shows bound DOX in the droplet shells.

DOX-loaded 1% PFCE or PFP emulsions were centrifuged and resuspended in PBS to remove the excess micelles in the solution. A drop of the solution was placed on a glass slide and fluorescence of DOX bounded to the droplets was examined using an inverted confocal microscope (Olympus IX81, Olympus America Inc., Center Valley, Pa.), with 60×/1.45-standard oil immersion eyepiece (FIG. 13). DOX was excited with 488 nm argon laser illumination, and the fluorescence emission was detected through 570 nm bandpass emission filter. The images were processed using ImageJ software. DOX fluorescence was observed around the droplets, indicating that DOX was bound to the copolymer coating of the droplets. The size distributions of micellar and nanodroplet structures were dependent on the concentration of the copolymers. The average droplets' size was significantly smaller for high copolymer concentration compared with low copolymer concentrations. When the concentration of surfactant is high, there is sufficient number of surfactant molecules to cover the large interfacial area in emulsions composed of smaller droplets. Size distribution of PEG-PCL stabilized droplets was also dependent on the type of perfluorocarbon; PFCE droplet sizes were smaller than those of PFP droplets. PFCE has a larger molecular weight and higher boiling point than PFP and therefore more stable than PFP.

PEG-PCL copolymer was chosen for DOX loading, because it offers good biocompatibility and good permeability to many therapeutic drugs. DOX was physically entrapped in the micelles via hydrophobic interactions with the hydrophobic core of micelles. Upon introduction of perfluorocarbon into copolymer solution and emulsification, doxorubicin was partly transferred from micelles to the droplet surface. For 1.4% (w/v) copolymer concentration and 2% (v/v) PFCE concentration, doxorubicin partitioned between micellar structures and droplet surface, with 15% loading into droplets. DOX partitioning did not depend on the type of perfluorocarbon compound that formed droplet cores.

b. In Vitro Studies with Cultured Ovarian Cancer

Cell Culture.

A2780 ovarian drug sensitive cancer cells and A2780 MDR drug resistant cells were cultured in RPMI-1640 medium (Sigma Aldrich, St Louis, Mo.) with 10% heat deactivated fetal bovine serum (FBS) (USA Scientific Inc., Orlando, Fla.) and 1% penicillin-streptomycin (Sigma Aldrich, St Louis, Mo.). The cells were maintained at 37° C. in a humidified atmosphere with 5% $CO_2$.

Confocal Imaging of Ovarian Cancer Cells.

A2780 cells were grown on cover glass in an 8 well cover glass chamber (LabTek chambered cover glass, NUNC, Rochester, N.Y.), and incubated with either, DOX dissolved in PBS, DOX-loaded 1.4% PEG-PCL micelle solution, or DOX-loaded 1% PFCE or PFP emulsions. Hoechst 33258 (Sigma Aldrich, St Louis, Mo.) stain was used to identify the nuclei of the A2780 cancer cells. Confocal fluorescent images of the cells were obtained using inverted confocal microscope (Olympus IX81, Olympus America Inc., Center Valley, Pa.); and the images were processed using ImageJ software. Emission filters of 570 nm for DOX and 480 nm for Hoechst were selected for imaging. In some experiments, DAPI was added to stain the cells before incubation with DOX and ultrasound exposure as discussed below.

Sonication of Suspended Cells.

A2780 cells were lifted off the culture T-flasks with 1× Trypsin (0.25% trypsin, 0.02% EDTA, Sigma Aldrich, St Louis, Mo.). The cells were resuspended in media. This suspension was mixed 2:1 volume ratio with DOX-containing formulations with typical cell concentrations of $5.7 \times 10^6$ cells/mL. Two types of DOX solutions in PBS were used: hydrophilic hydrochloride salt DOX-HCl (20 µg/mL) or deprotonated DOX; the concentration in PBS was 20 µg/mL for either molecule. DOX formulations included deprotonated DOX incorporated in 1.4% PEG-PCL micellar solution or DOX incorporated in 1% PFCE or PFP PEG-PCL emulsion; DOX concentration was the same as in PBS solutions (20 µg/mL). The cell suspensions were sonicated in a Samco transfer pipette (Samco Scientific Corporation, CA), with ultrasound generated by Omnisound 3000 instrument (Accelerated Care Plus Inc, Sparks, Nev.); 1-MHz continuous wave (CW) or pulsed ultrasound with 33% duty cycle was delivered at 3.4 W/cm$^2$ nominal power densities, which corresponded to the 1.18 MPa actual peak-to-peak ultrasound pressure at the site of the sample; 3-MHz ultrasound was applied at 2 W/cm$^2$ nominal power density, corresponding to 1.7 MPa actual peak-to-peak ultrasound pressure at the site of the sample. The probe and the pipette, with a distance of 0.5 cm between them, were immersed in a water bath maintained at 37° C. Ultrasound exposure was 60 s for CW ultrasound and 180 s for pulsed ultrasound which provided for the same total ultrasound exposure. Pressure was measured using ONDA needle hydrophone (Onda HNR-0500) (calibrated in October, 2009) placed in front of the probe with a distance of 0.5 cm from the probe. Prior to sonication, cell suspensions in the desired formulation were incubated for 20 minutes at 37° C. After ultrasound treatments, a droplet of the cell suspension was placed on a glass slide, and the fluorescence inside the cells was observed and quantified using confocal microscope as described above.

Sonication of Cells Attached to Substrate and Gel Experiments.

A2780 cells were grown in 10 mL capacity OptiCell units (Biocrystal, Westerville, Ohio) to 90% confluence, upon which the cells were stained with 4', 6-diamidino-2-phenylindole (DAPI) (Sigma Aldrich, St. Louis, Mo.). Concentration of DAPI was 140 µg/mL. After incubation for 30 minutes, the media in opticell was replaced with 1.2% (w/v) agarose solution containing either DOX loaded micelle solution or DOX loaded PFCE droplet suspension prepared as described below.

The initial agarose solution was formed by dissolving the agarose (Agarose II, GBiosciences, Maryland Heights, Mo.) in PBS, heated to 100° C. The gelling temperature of Agarose II was 24-28° C. The sample of micelle or PFCE droplets was added after the solution cooled to 37° C. DOX loaded formulations were added to the gel solution (total volume 10 mL), with the final concentration of DOX (4 µg/mL) encapsulated in 0.28% PEG-PCL micellar solution or 0.4% PFCE/0.28% PEG-PCL droplet suspension. The solutions at 37° C. gelled within 5 minutes after injection into the opticell unit. For each sample, a control opticell was not sonicated. The opticells with either PBS, micelles, or PFCE droplets were sonicated at 25° C. with 1-MHz or 3-MHz ultrasound; CW or pulsed ultrasound of various frequencies were applied to different marked regions of the same opticell separated by at least 2 cm from each other. Ultrasound exposure was 30 s for CW ultrasound and 90 s for pulsed ultrasound which provided for the same total ultrasound exposure. After sonication, cells were imaged using confocal microscopy. Emission filters of 570 nm for DOX and 480 nm for DAPI were selected for imaging.

Incubation of Ovarian Cancer Cells with DOX Dissolved in PBS, DOX Loaded Micelles and Droplets.

Figure 15:
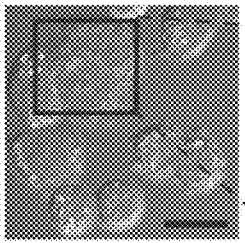
FIG. 15 shows confocal images of substrate-attached A2780 ovarian cancer cells incubated with (i) Hoechst stain (indicates the nuclei of the cells), (ii) DOX encapsulated in micelles, (iii) DOX encapsulated in PFCE droplets; and (iv) DOX encapsulated in PFP droplets. Scale bar is 20 μm. R/G ratios of the cell fluorescence were averaged over the cells in FOV and tabulated below the Figure. The brightness and contrast of magnified insets of the images were modified to reveal if DOX penetrated into cell nuclei.

A2780 drug sensitive cells, grown on chambered cover slip were incubated with different DOX formulations and confocal fluorescent images were obtained (FIGS. 14 and 15). Different image slices of the cell layer attached to the cover slip were recorded at an incremental step of 0.5 µm depth from the bottom to top of the cell layer (z-direction). The images recorded were stacked in z-direction and processed using ImageJ. The brightness and contrast ratios of magnified insets of the images were modified to reveal the intracellular distribution of fluorescence. FIG. 14 shows cells incubated with Hoechst stain; cells have their nuclei stained blue. The cells incubated with hydrophilic DOX dissolved in PBS (20 µg/mL DOX) showed red fluorescence in the nuclei indicating that the free DOX in the solution is able to enter the nuclei of the A2780 cells. When the cells were incubated with deprotonated DOX at the same DOX concentration, the DOX did not get into the nuclei (FIG. 14) as well as the fluorescence inside the cell was low compared to hydrophilic DOX, indicating low cellular uptake of hydrophobic DOX. It is known that the hydrophobic drugs with high partition coefficients are preferentially distributed to hydrophobic compartments such as lipid bilayers of cells. Note that deprotonated DOX was used for incorporation into micelles and droplets. The deprotonated DOX that is protected by the micelles and droplets with the hydrophilic coating behaves differently than the free deprotonated DOX, and we observe a higher uptake of DOX by the cells with micelles compared to free deprotonated DOX.

DOX fluorescence inside the cells was characterized by the R/G ratio where R is the intensity of red color and G is that of green color at the same region of interest (ROI) inside the cells. This ratio is used because DOX absorbs green light that ignites its red fluorescence. The R and G values and ratios were measured using ImageJ software.

For cells incubated with DOX encapsulated in PEG-PCL micelles or PFCE (or PFP) emulsions, fluorescence was mostly localized outside of cell nuclei indicating that DOX trafficking into the nuclei was inhibited. The red/green (R/G) ratio of the fluorescence inside the cells and R/G ratio of the background fluorescence from the cover slip were measured. Background value was subtracted from the cell's R/G ratio. The R/G values for cells treated with different formulations are tabulated below the images in FIG. 15. The cells incubated with either PFCE or PFP droplets have lower fluorescence (R/G ratios of 0.31 and 0.14 for PFCE and PFP respectively) than the cells incubated with DOX in micellar solution (R/G ratio of 0.63). The presence of perfluorocarbon droplets reduced the intracellular DOX uptake even though DOX loaded micelles was in excess in the emulsion solution. This may be related to differences in micelle properties in the presence or absence of PFCs. Micelle cores dissolve some perfluorocarbon even at very low perfluorocarbon concentration, micellar solutions appear to be much more hydrophobic than solutions of "pure" micelles. This may alter copolymer block conformations and micelle ability to diffuse through plasma membranes (or alter endocytosis efficiency).

Effect of the Ultrasound Treatment of Cells in Suspensions in the Presence and Absence of Droplets.

Figure 16:
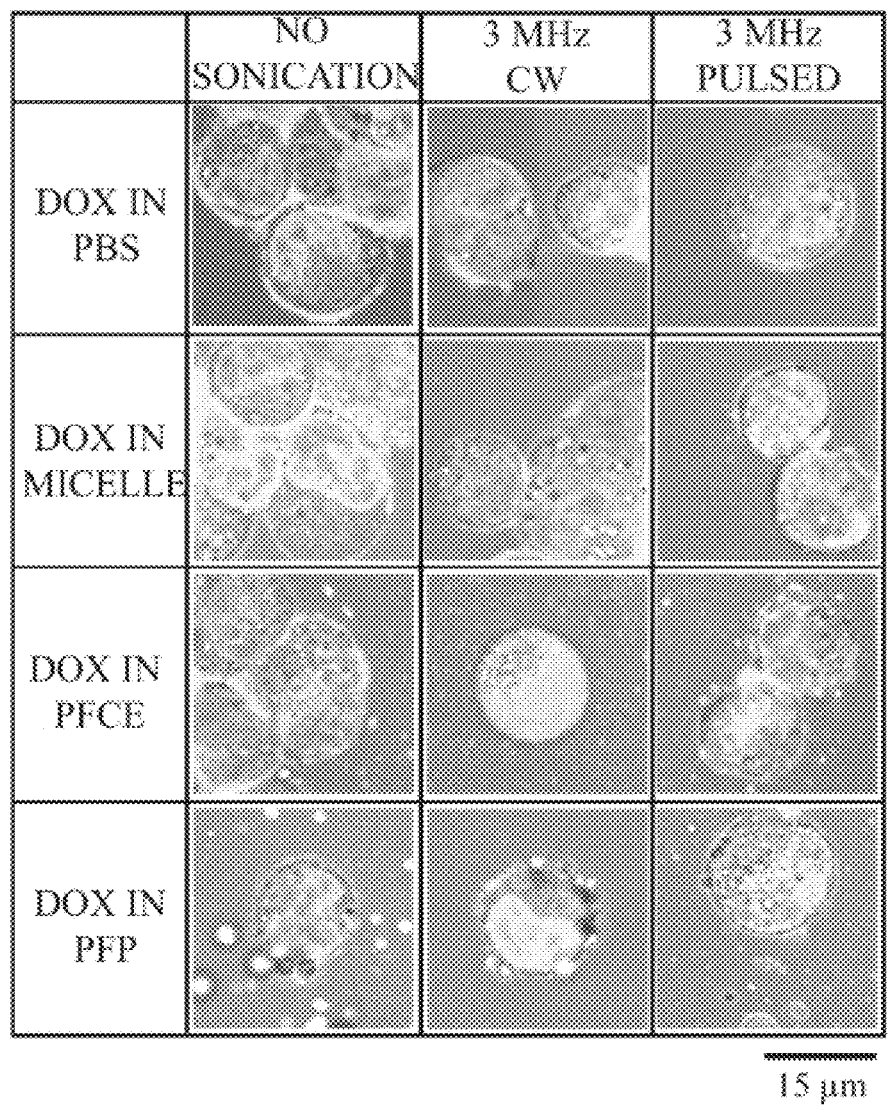
FIG. 16 shows confocal images of suspended ovarian cancer A2780 cells treated with either free DOX, DOX encapsulated in micelle, DOX encapsulated in PFCE or PFP droplets, without and with ultrasound treatment by 3-MHz continuous wave (CW) or pulsed ultrasound. Hoechst fluorescence is shown as green and DOX fluorescence as red. When Hoechst and DOX fluorescence overlay, yellow color is generated. The color of the nuclei changes from green to yellow when DOX is taken up by the nuclei.

A2780 drug sensitive cells suspended in media were mixed with hydrophobic DOX in PBS, DOX loaded micellar solution, PFCE or PFP emulsion and treated with various ultrasound parameters: i) No sonication ii) unfocused 3 MHz Continuous wave US and iii) unfocused 3 MHz pulsed ultrasound (Duty cycle 33%). The final concentration of DOX in all cell suspension samples was 10 µg/mL. PEG-PCL concentration was 0.7%; for droplets, PFCE and PFP concentrations were 1% (v/v). After treatment, both unsonicated and sonicated cell suspensions were stained with Hoechst and imaged with confocal microscope. Image processing was performed using ImageJ. FIG. 16 shows composite images of both Hoechst and DOX fluorescence inside the cells, with Hoechst shown as green color so that the overlap of green color of Hoechst and red fluorescence of DOX can be identified as yellow color in composite images, which will indicate DOX penetration into cell nuclei. Even without sonication, images of cells incubated with micelles show some DOX penetration into cell nuclei which is different from previously observed negligible fluorescence inside the nuclei of attached cells. A 3-MHz CW ultrasound treatment somewhat enhanced DOX penetration into cell nuclei for all samples. The effect of ultrasound on DOX in PBS or DOX in micellar solution was marginal. The strongest effect was observed in the presence of either PFP or PFCE droplets, with cell nuclei turning bright yellow. The effect of pulsed ultrasound of the same overall energy was lower than that of CW ultrasound indicating the role of thermal effects in enhanced DOX trafficking into cell nuclei.

Figure 17:
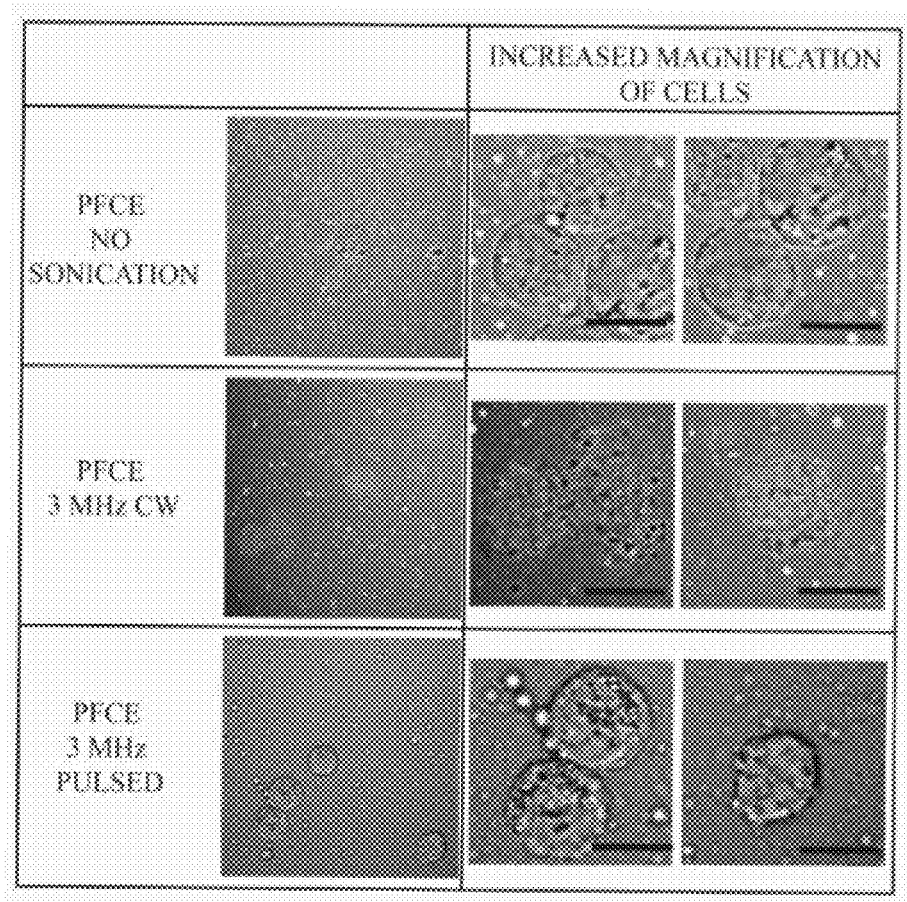
FIG. 17 shows laser confocal images of suspended ovarian cancer A2780 cells incubated with DOX loaded PFCE droplets in suspensions. Sonication in the presence of PFCE droplets caused disruption of cell membrane, enhanced intracellular DOX uptake and enhanced DOX penetration into cell nuclei. The effect was stronger for CW compared with pulsed ultrasound. Scale bar is 15 μm.

The number of PFP droplets decreased significantly after ultrasound treatment. No droplet sticking to cell membranes was observed before sonication. A few PFP droplets were found sticking to the cell membranes after sonication. Droplet sticking to the cells may cause damage to cell membranes due to bubble cavitation after droplet-to-bubble transition. Another example of the effect of 3 MHz CW and pulsed ultrasound on suspended A2780 cells in the presence of PFCE droplet is shown in FIG. 17. Exposure to 3 MHz CW ultrasound in the presence of droplets caused rupture of cell membranes, which was pronounced for PFCE compared with PFP droplets. The number of PFCE droplets decreased after sonication, though much less than was observed for PFP droplets. The major effect on droplets was related to droplet coalescence into larger droplets. The effect of CW ultrasound was stronger than that of pulsed ultrasound as shown for the PFCE droplets.

Effect of Ultrasound Delivered Through Agarose Gel on the Cells Attached to the Substrate.

Figure 18:
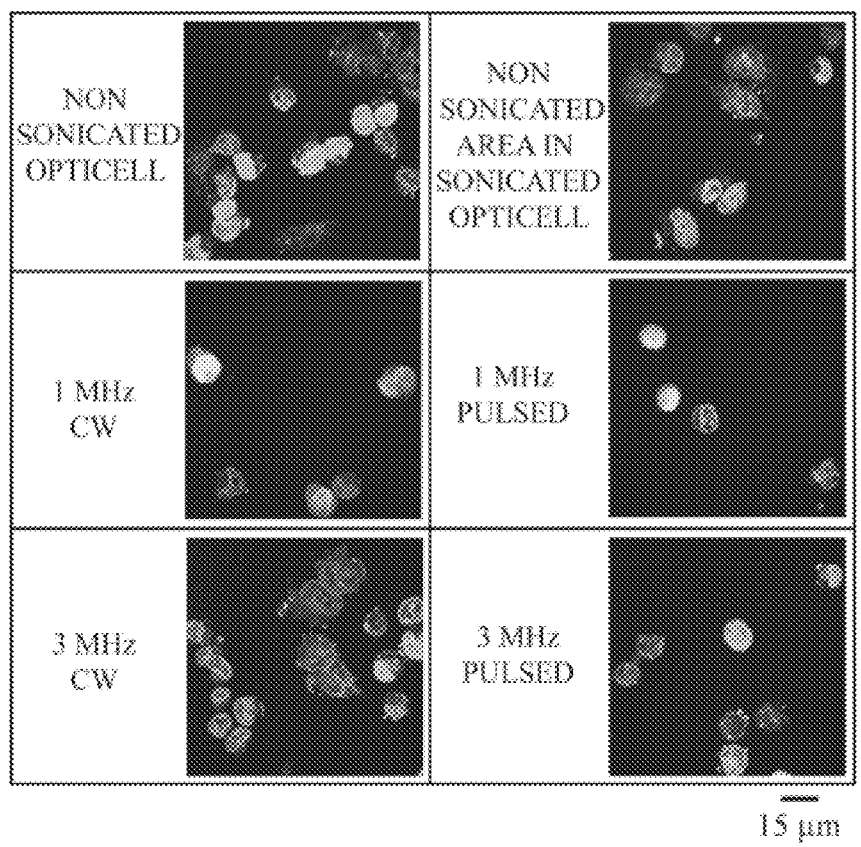
FIG. 18 shows laser confocal images of substrate-attached A2780 ovarian cancer cells treated with CW or pulsed 1-MHz or 3-MHz ultrasound delivered through the agarose gel impregnated with DOX-loaded micelles. 1-MHz ultrasound induced significant reduction in number of cells and significant enhancement of DOX penetration into cell nuclei. No significant effect of 3-MHz ultrasound was observed.
Figure 19:
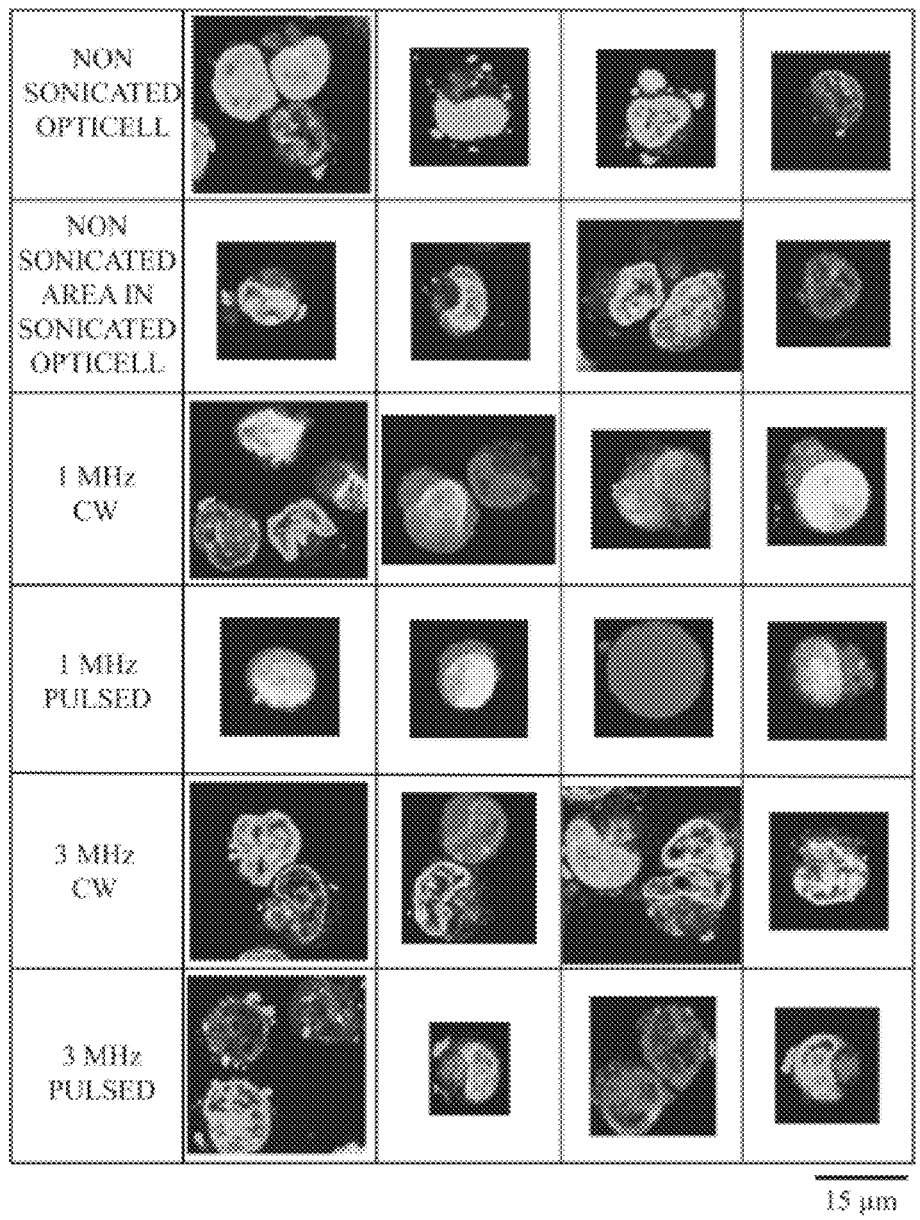
FIG. 19 shows magnified laser confocal images of substrate attached A2780 ovarian cancer cells treated with 1-MHz or 3-MHz ultrasound delivered through the agarose gel impregnated with DOX-loaded micelles.
Figure 20:
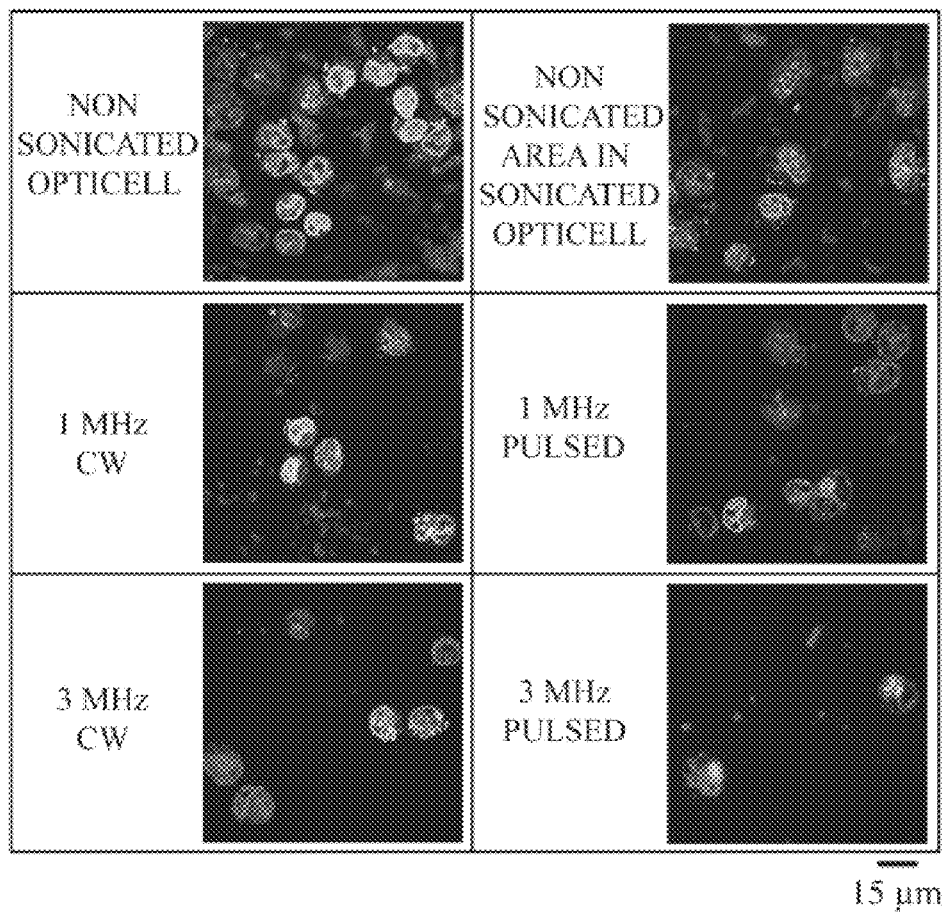
FIG. 20 shows laser confocal images of substrate attached A2780 ovarian cancer cells treated with 1-MHz or 3-MHz ultrasound delivered through the agarose gel impregnated with DOX-loaded PFCE droplets. Image shows significant reduction in number of cells after ultrasound treatment.

The A2780 drug sensitive cells attached to the opticell membrane were treated with either micelle solution or PFCE droplet suspension immobilized in agarose gel inside the opticell chamber. Control opticell with micellar or PFCE droplet suspension was not sonicated. Small areas in the opticells with micelles or PFCE droplets were sonicated with either 1-MHz, 3-MHz, CW or pulsed ultrasound (duty cycle 33%). Cells were stained with DAPI prior to sonication. DAPI is a fluorescent stain that binds strongly to DNA, and can pass through intact cell membranes. DAPI penetration through intact cell membranes is not very efficient, which allows staining of only a fraction of cell population, which is advantageous for interpretation of results. FIGS. 18 and 19 shows confocal images of cells in the opticell that were either non-sonicated or sonicated with DOX encapsulated in PEG-PCL micellar solution impregnated into the gel. The strongest effect on the cells sonicated through the micelle-impregnated agarose gel was for 1-MHz sonication compared to 3-MHz ultrasound, which was true for both CW and pulsed ultrasound. FIG. 20 shows significant reduction in the number of cells with 1-MHz sonication. DAPI fluorescence is shown as green, so when DOX is taken up in the cell nuclei, the combination of green and red in the nuclei can be easily visualized as yellow. In the presence of micelles, 1 MHz ultrasound significantly enhanced transport of DOX into the cell nuclei, while 3 MHz ultrasound in the presence of micelles did not affect DOX intracellular distribution (FIG. 19).

Figure 21:
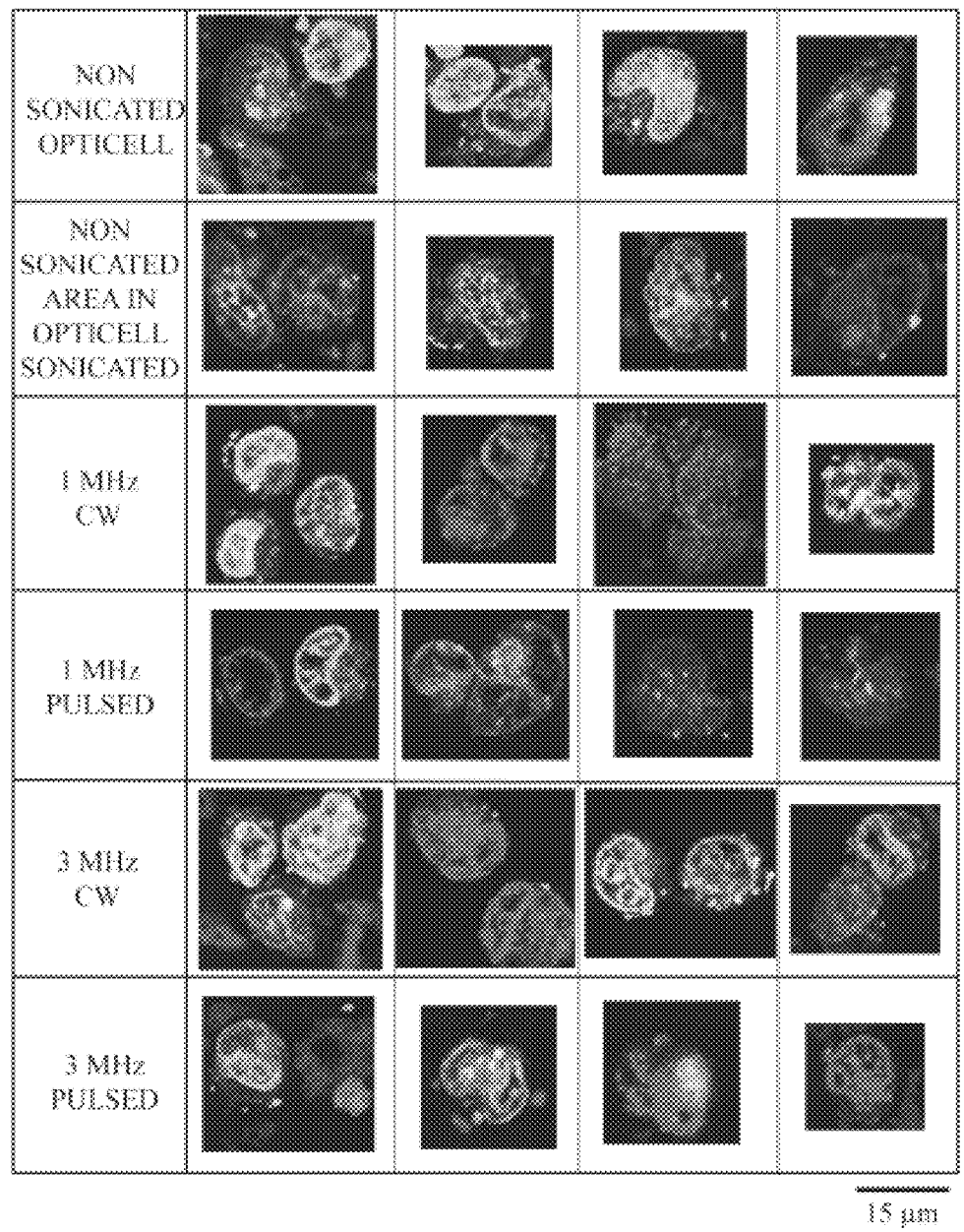
FIG. 21 shows magnified confocal images of substrate attached A2780 ovarian cancer cells treated with 1-MHz or 3-MHz ultrasound delivered through the agarose gel impregnated with DOX-loaded PFCE droplets. In the presence of nanodroplets, the effect of 3-MHz ultrasound is stronger than that of 1-MHz ultrasound.

Similarly, FIGS. 20 and 21 show confocal images of the cells that were sonicated in the presence of PFCE droplets. Both 1 MHz and 3 MHz sonication reduced the number of the cells (FIG. 21), with 3 MHz treatment being the most effective. DOX trafficking into the nuclei was also higher for 3-MHz compared with 1-MHz ultrasound.

Based on the data presented above, it was concluded that the dependence of cellular effects on ultrasound frequency is different for micelles and droplets. For DOX encapsulated in micelles, 1-MHz US is more efficient than 3 MHz US in cancer cell killing and promoting nuclear DOX uptake drug uptake, whereas opposite frequency dependency is observed for DOX encapsulated in droplets.

c. Discussion

Doxorubicin-loaded perfluoropentane and perfluoro-15-crown-5-ether droplets stabilized with poly (ethylene glycol)-co-polycaprolactone (PEG-PCL) copolymer shell were explored for their ultrasound-mediated drug delivery properties. Cell culture experiments using ovarian carcinoma A2780 cells showed that without ultrasound, the intracellular DOX uptake was lower for DOX encapsulated in nanodroplets compared to DOX encapsulated in micelles. This is advantageous for preventing DOX interaction with healthy tissues. The intracellular DOX uptake was enhanced by ultrasound application. Ultrasound also affected the intracellular DOX trafficking, favoring nuclear accumulation of anthracycline drug needed for efficient chemotherapeutic action.

With micellar formulations, 1 MHz ultrasound caused a strong effect on DOX trafficking into cell nuclei and reduction in cell number indicating immediate ultrasound induced cell killing, whereas 3 MHz ultrasound did not cause any considerable effects. This was true for both suspended or attached cells. In contrast, for the nanodroplet formulations, the effect of 3-MHz ultrasound was stronger than that of 1-MHz ultrasound.

Figure 22:
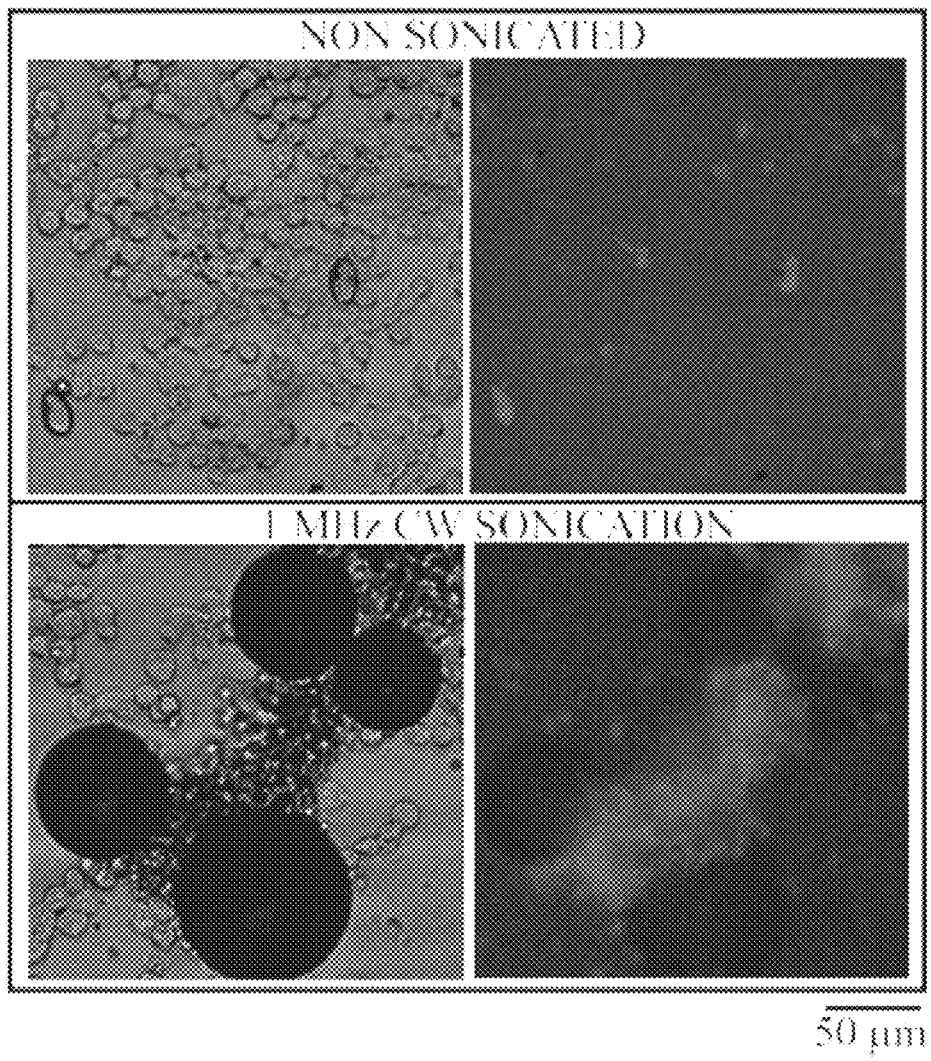
FIG. 22 shows fluorescent images of the multi-drug resistant ovarian cancer cells treated with 1-MHz CW sonication in the presence of air bubbles. Comparison of a phase contrast (left) and fluorescence (right) image shows enhanced DOX uptake by the cells located in the ultrasound field between the bubbles.

In the presence of nanodroplets, significant ultrasound-induced cell sonoporation was observed while no sonoporation was observed during sonication of micellar solutions. The difference between sonoporation effects in the presence and absence of droplets is most probably related to ultrasound induced droplet to bubble transition and cavitation of bubbles formed. The role of bubble cavitation in intracellular uptake of DOX by cells can be illustrated by a model experiment shown in FIG. 22. Air bubbles were introduced into the Opticell containing multidrug resistant (MDR) A2780/AD ovarian cells attached to the substrate. The cells were treated with 1 MHz ultrasound (power density, 3.4 W/cm$^2$) in the presence of 1.4% DOX loaded PEG-PCL micelle solution. The ultrasound field between the bubbles caused cell detachment from the substrate and dramatically enhanced DOX uptake by multidrug resistant (MDR) ovarian carcinoma cells, compared to cells that were not sonicated. The cells at a distance from the bubbles, though sonicated, remained attached to the substrate and manifested much lower, if any DOX uptake.

Comparison of PFP and PFCE droplets show that the effect of PFP droplets on DOX uptake and nuclear trafficking was stronger than for PFCE droplets. This may be related to larger sizes of PFP droplets, easier droplet to bubble transition, and larger size of PFP bubbles that would move faster under radiation force and exert higher damage of the cells they collide with. However PFP droplets present a problem as drug carriers. The main problem is associated with their stability and handling problems. Also, droplet-bubble transition that occurs during injection through fine gauge needles is hard to control. Taking into consideration these problems and the fact that PFCE droplets manifest high activity in DOX delivery, PFCE nanoemulsions should be preferred as drug carriers for ultrasound-mediated drug delivery. In addition, only PFCE and not PFP droplets offer a great advantage of $^{19}$F MR imaging of nanodroplet biodistribution.

It is important to outline that the effect on nuclear trafficking and cell killing in the presence of nanodroplets was observed for both CW and pulsed ultrasound. For CW ultrasound, both thermal and mechanical components of ultrasound were operative while for pulsed ultrasound, at our power densities and sonication duration, the effect of ultrasound was predominantly mechanical. The data imply that both thermal and mechanical modes of action are operative in ultrasound-mediated drug delivery.

Enhanced doxorubicin uptake by the A2780 ovarian cancer cells, nuclear DOX transport, and cell membrane damage were observed when cells were treated with micellar or nano-droplet encapsulated DOX in combination with 1 MHz or 3 MHz ultrasound. Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A nanoemulsion comprising (1) at least one perfluoro crown ether and (2) polyethylene glycol poly(d,l)lactic acid block copolymer, wherein the nanoemulsion comprises a therapeutic agent encapsulated in the nanoemulsion.

2. The nanoemulsion of claim 1, wherein the perfluoro crown ether is perfluoro 12-crown-4 ether, perfluoro 15-crown-5 ether, perfluoro 18-crown-6 ether, perfluoro 20-crown-7 ether, perfluoro dibenzo-18-crown-6 ether, perfluoro diaza-18-crown-6 ether, or any combination thereof.

3. The nanoemulsion of claim 1, wherein the perfluoro crown ether is perfluoro 15-crown-5 ether.

4. The nanoemulsion of claim 1, wherein the therapeutic agent comprises a chemotherapeutic drug.

5. The nanoemulsion of claim 1, wherein the therapeutic agent comprises paclitaxel, doxorubicin, gemcitabine, adriamycin, cisplatin, taxol, methotrexate, 5-fluorouracil, betulinic acid, amphotericin B, diazepam, nystatin, propofol, testosterone, estrogen, prednisolone, prednisone, 2,3 mercaptopropanol, progesterone, or any combination thereof.

6. The nanoemulsion of claim 1, wherein the therapeutic agent comprises paclitaxel, doxorubicin, or any combination thereof.

7. The nanoemulsion of claim 1, further comprising at least one polyoxyethylene-polyoxypropylene-polyoxyethylene triblock copolymer.

8. A pharmaceutical composition comprising the nanoemulsion of claim 1 and a pharmaceutically acceptable carrier.

9. A method for treating a tumor comprising the steps:
  (a) contacting the tumor with the nanoemulsion of claim 1, wherein the therapeutic agent comprises a chemotherapeutic agent; and
  (b) exposing the tumor to ultrasonic radiation.

10. The method of claim 9, wherein the ultrasonic radiation comprises from about 30 kHz to about 20 MHz.

11. The method of claim 9, wherein the tumor is a multi-drug resistant tumor.

12. The method of claim 9, wherein the tumor is breast cancer, pancreatic cancer, ovarian cancer, prostate cancer, or colon cancer.

13. The method of claim 9, further comprising imaging the tumor by $^{19}F$ MRI.

14. A method of treating a cancer in a subject comprising
  i. administering the nanoemulsion of claim 1 to the subject, wherein the therapeutic agent comprises a chemotherapeutic agent; and
  ii. exposing a tumor present in the subject to ultrasonic radiation.

15. The method of claim 14, wherein the nanoemulsion is administered systemically to the subject by injection.

16. The method of claim 14, further comprising imaging the tumor imaged by $^{19}F$ MRI.

17. A method for treating a tumor comprising the steps:
  i. contacting the tumor with the nanoemulsion of claim 1, wherein the therapeutic agent comprises a chemotherapeutic agent;
  ii. imaging the tumor by $^{19}F$ MRI to identify the location of the nanoemulsion in the tumor; and
  iii. exposing the tumor to ultrasonic radiation.

18. The method of claim 17, wherein in step (b) the tumor is further imaged by $^{1}H$ MRI.

19. The method of claim 17, wherein the ultrasonic radiation is unfocused ultrasound or focused ultrasound (FUS).

20. A method for delivering a therapeutic agent to the nucleus of a tumor cell comprising the steps:
  i. contacting the tumor cell with the nanoemulsion of claim 1; and
  ii. exposing the tumor cell to ultrasonic radiation.

* * * * *

UNITED STATES PATENT AND TRADEMARK OFFICE
CERTIFICATE OF CORRECTION

PATENT NO. : 8,709,451 B2
APPLICATION NO. : 13/008951
DATED : April 29, 2014
INVENTOR(S) : Kweon-Ho Nam and Natalya Y. Rapoport Page 1 of 1

It is certified that error appears in the above-identified patent and that said Letters Patent is hereby corrected as shown below:

In the Specification

Please replace the paragraph at column 1, lines 16-18 with the following paragraph:

This invention was made with government support under grant number R01 EB001033 awarded by National Institutes of Health. The government has certain rights in this invention.

Signed and Sealed this
Seventh Day of July, 2015

Michelle K. Lee
*Director of the United States Patent and Trademark Office*